United States Patent
Wu

(10) Patent No.: US 7,997,119 B2
(45) Date of Patent: Aug. 16, 2011

(54) CHEMICAL SAMPLING AND MULTI-FUNCTION DETECTION METHODS AND APPARATUS

(75) Inventor: Ching Wu, Acton, MA (US)

(73) Assignee: Excellims Corporation, Acton, MA (US)

( * ) Notice: Subject to any disclaimer, the term of this patent is extended or adjusted under 35 U.S.C. 154(b) by 257 days.

(21) Appl. No.: 11/736,233

(22) Filed: Apr. 17, 2007

(65) Prior Publication Data

US 2008/0250877 A1 Oct. 16, 2008

Related U.S. Application Data

(60) Provisional application No. 60/767,494, filed on Apr. 18, 2006, provisional application No. 60/896,024, filed on Mar. 21, 2007.

(51) Int. Cl.
*G01N 7/00* (2006.01)
*G01N 27/72* (2006.01)

(52) U.S. Cl. ......... 73/31.03; 73/31.01; 73/31.02; 73/31.05; 324/239

(58) Field of Classification Search ........... 73/863, 73/863.01, 863.11, 863.12, 863.21, 863.22, 73/863.23, 864.71, 864.81, 864.83, 864.91, 73/31.01–31.05; 324/239
See application file for complete search history.

(56) References Cited

U.S. PATENT DOCUMENTS

| | | | |
|---|---|---|---|
| 4,423,377 A * | 12/1983 | Podhrasky | 324/329 |
| 4,580,440 A * | 4/1986 | Reid et al. | 73/31.07 |
| 4,909,090 A | 3/1990 | McGown | |
| 5,027,643 A * | 7/1991 | Jenkins | 73/23.39 |
| 5,092,157 A | 3/1992 | Achter | |
| 5,123,274 A | 6/1992 | Carroll | |
| 5,465,607 A | 11/1995 | Corrigan | |
| 5,551,278 A * | 9/1996 | Rounbehler et al. | 73/1.06 |
| 5,942,699 A * | 8/1999 | Ornath et al. | 73/863.21 |
| 5,970,803 A | 10/1999 | Staples | |
| 6,269,703 B1 | 8/2001 | Bowers | |
| 6,333,631 B1 * | 12/2001 | Das et al. | 324/326 |
| 6,354,160 B1 * | 3/2002 | Staples et al. | 73/863.12 |
| 6,378,385 B1 * | 4/2002 | Bowers | 73/863.12 |
| 6,386,015 B1 * | 5/2002 | Rader et al. | 73/31.05 |
| 6,477,907 B1 * | 11/2002 | Chambers et al. | 73/866 |
| 6,559,645 B2 * | 5/2003 | Arndt et al. | 324/329 |
| 6,610,977 B2 * | 8/2003 | Megerle | 250/287 |
| 6,651,520 B1 * | 11/2003 | Allen et al. | 73/863.81 |
| 6,656,738 B1 * | 12/2003 | Vogel et al. | 436/161 |
| 6,888,128 B2 | 5/2005 | Krasnobaev | |
| 6,891,477 B2 * | 5/2005 | Aronstam | 340/606 |
| RE38,797 E * | 9/2005 | Linker et al. | 73/863.12 |
| 6,978,657 B1 | 12/2005 | Baumann | |
| 7,299,679 B2 * | 11/2007 | Lovell et al. | 73/31.05 |
| 7,306,649 B2 * | 12/2007 | Boyle et al. | 95/82 |
| 2003/0085348 A1 * | 5/2003 | Megerle | 250/287 |
| 2004/0119475 A1 * | 6/2004 | Earle | 324/329 |
| 2006/0042407 A1 * | 3/2006 | Napoli | 73/863.12 |
| 2006/0115559 A1 * | 6/2006 | Jones, Jr. | 426/231 |
| 2006/0243071 A1 * | 11/2006 | Sagi-Dolev | 73/865.8 |
| 2006/0249671 A1 | 11/2006 | Karpetsky | |

(Continued)

*Primary Examiner* — David A. Rogers

(57) ABSTRACT

This invention describes a sample collection method that could release and collect residues of explosives and other chemicals from a surface; the described method is implemented into a compact detection system that can be used as a "wand" for screening chemicals residues on a subject. The wand configuration includes multi-function for sampling and detecting multiple threads. The invention further describes a method of inspecting a subject using an interrogating apparatus in a sweeping motion; the near range closed loop particle sampling arrangement allows effective collection of particle and vapor residues from a targeted surface. The invention also describes a sampling and detecting apparatus for on-the-fly threat detection using compact ion mobility based detectors.

9 Claims, 19 Drawing Sheets

U.S. PATENT DOCUMENTS

| | | |
|---|---|---|
| 2007/0034024 A1 | 2/2007 | Syage |
| 2007/0068284 A1* | 3/2007 | Castro et al. ............... 73/863.21 |
| 2007/0086925 A1* | 4/2007 | O'Donnell et al. ........... 422/100 |
| 2007/0114382 A1 | 5/2007 | Clemmer |
| 2007/0114389 A1 | 5/2007 | Karpetsky |
| 2008/0179522 A1* | 7/2008 | Vallon et al. ............... 250/336.1 |

* cited by examiner

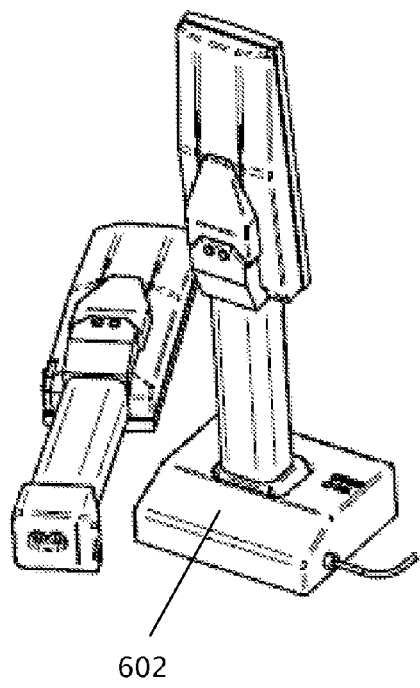 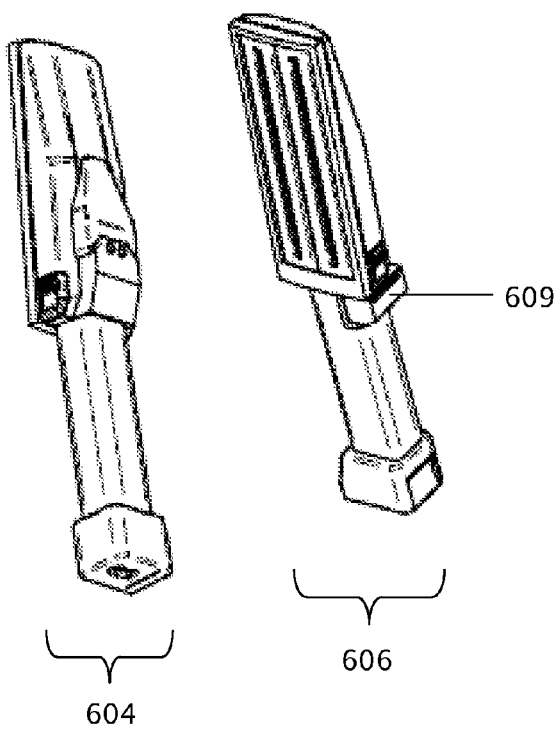
Figure 6A
Figure 6B

Configuration I    Configuration II    Configuration III

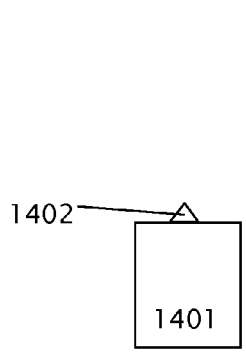
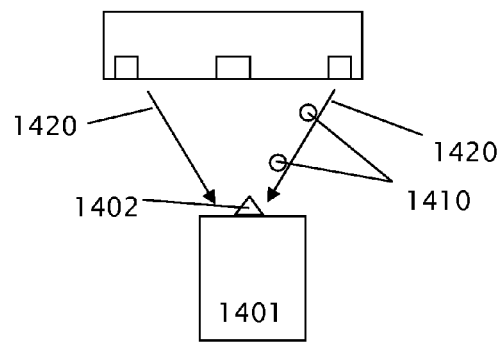
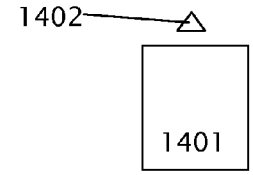
Figure 14A    Figure 14B    Figure 14C
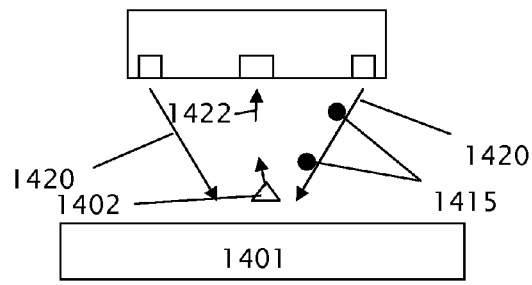
Figure 14D

CHEMICAL SAMPLING AND MULTI-FUNCTION DETECTION METHODS AND APPARATUS

CROSS-REFERENCE TO RELATED APPLICATIONS

The present application claims the benefit of and priority to corresponding U.S. Provisional Patent Application Nos. 60/767,494 and 60/896,024, filed Apr. 18, 2006 and Mar. 21, 2007 respectively, the entire content of the applications are herein incorporated by reference.

BACKGROUND OF THE INVENTION

Increasingly, explosives and other chemical warfare agents have become paramount threats to screen for in airports and government buildings. With access to plastic explosives and skillful disguising of weapons and explosive devices as ordinary, innocuous objects, terrorists need to be identified from the general passengers boarding aircraft or entering government buildings. It is known that certain explosive materials are inherently sticky, such as C-4 (a RDX based explosive) and can be removed from luggage or objects by physically touching (wiping) a sampling trap across the surface and then inserting the sampling trap in a detector such as an ion mobility spectrometer for analysis. Screening of people is a more difficult challenge since the above screening technique used on luggage is too intrusive and may violate human rights. A more socially acceptable screening method is to collect the chemical particle or vapor on a sampling trap without contacting the person.

By deploying the trace detection portal systems into airport check points, non-contact detection of explosives from airline passengers has gradually become possible. Currently, the trace detection portal systems are under some pressure to improve the efficiency of dislodging and collecting explosive particles from human body. In this invention, we describe a sample collection/detection method that could release and collect residues of explosives and other chemicals more effectively. Instead of using a large scale air handling system to release, collect, transport samples to the detection system as those used in trace detection portals, a sampling system in close proximity to the target area such as a handheld "wand" is described herein for screening chemical residues on the human body.

The concept of a using a handheld "wand" is a well accepted concept at security check points. Handheld metal detectors are still the best way to search for weapons on selectees when they cause an alarm at the walkthrough metal detector. This invention describes a handheld wand that can be used to confirm an alarm from the trace detection portal systems. In addition, flexibility and portability of the handheld wand will extend its application to broader security related areas, especially where a trace detection portal is not available. The handheld wand can be used as an intermediate step before a complete manual search is performed. Additionally, the handheld wand can be combined with multiple detectors for searching multiple threats. An exhaustive search for multiple threats can save valuable time and effort.

SUMMARY OF THE INVENTION

When a terrorist prepares explosive devices, trace amounts of the explosive inevitably clings to the person's skin and/or clothing. An advantage to performing a search with a handheld wand over detection portal systems is the ability to position the wand over a desirable location on the individual. This is contrary to the detection portal systems where the air jets are in a fixed position and screening for different size or height individuals may miss a desirable location on the individual. In addition, another advantage to performing a search with a handheld wand over detection portal systems is the process of collecting the particles. Since the collector is closer to the air jets in the handheld wand, the explosive particles and/or vapor is collected more effectively. This close proximity is also advantageous for other detecting devices that can be incorporated into the handheld wand, such as a metal detector or a Geiger counter.

The handheld wand can have many different configurations. The first having a sampling component, for sampling and preconcentration of chemicals in both particle and vapor form. This sampling configuration will allow for collecting explosives onto media such as a sample collector that is compatible with the current trace detection systems. The samples collected from the wand on the sample collector could be directly inserted into a detection system. Secondly, a configuration whereby the handheld wand is integrated with an onboard ion mobility based detector or other detection method, without significantly increasing the size and weight, could be optimized to detect explosives and other chemicals with higher systemic sensitivity compared to the portal systems. The handheld wand can be a rugged, battery operated detector that is intended to be used in the same fashion as the handheld metal detectors. Thirdly, a configuration where the handheld wand is used as a single device to search for multiple threats by combining the chemical sampling and/or detection components with other detectors to provide a multi-function detection wand.

This invention describes a dynamic inspection method that enables direct sampling of particles and/or vapors on the human body or other surfaces. The described chemical sampling and detection method is capable of releasing and extracting particles and vapors from the cloth, preconcentrating these samples in the wand, and/or detecting them in a few seconds with the onboard detection method, e.g. ion mobility spectrometer (IMS). It uses an air pump or pumps to generate both impinging and collecting air flows. Continuous or pulsed air jets are combined with adjacent suction ports to release and collect particles from clothing. In addition, with the handheld wand configuration, vapors can also be collected from the inner layer of the fabrics. Used in a close range from targeted samples, the handheld wand should have a better sample collection efficiency compared to the portal systems. The capability of being able to detect vapors under the clothing may address different kind threats that are not well detected by trace detection portals, i.e. a well packed hidden bulk amount of chemicals, such as explosives, on human body. As for explosive detection, most explosives do not have a very high vapor pressure to be detected in an open area, however, under one or multiple layers of clothing, the vapor pressure could reach a detectable range, especially, when the bulk materials are heated by body heat. Assuming the body temperature (~37° C.) is ten degrees above the environment temperature, the vapor pressure of explosives may increase 5 to 15 times [Yinon, Jehuda, Forensic and Environmental Detection of Explosives, John Wiley, Chichester, 1999].

Several approaches for screening people and/or objects have been developed in the past that involve collecting explosive particles and/or vapor using portable/handheld devices, however, they either contact the subject, or are not suitable for screening large surface areas rapidly, such as the human body. In order to not violate human rights, the more socially acceptable screening method is to not contact the person. Unlike the methods of using a handheld device for sampling by contacting the targeted area, the present invention provides a unique and effective way to dislodge and collect the particles in a non-contacting manner.

In addition to releasing particles with only the impinging air flow, since certain explosive materials are inherently sticky, such as C-4 (a RDX based explosive) and Deltasheet (a PETN based explosive), the temperature of the air flow or the addition of a doping substance into the airflow will assist in lifting and collecting the chemicals of interest. Due to the nature of the explosives and form they are produced, some explosive molecules are generally greasy substances and are hydrophobic. Methods used to lift and collect the particles of interest in this invention are to: (1) vaporize explosive molecules by heating, (2) minimize the explosive molecule electrostatics by increasing humidity by doping moisture in the air flow, thus neutralizing a charge imbalance or by doping plasma (ionized air) in the air flow, (3) separate the explosive molecule from the matrix by utilizing the intermolecular interactions that are exclusive to the explosive molecule (ionic interaction, hydrogen bonding, dipole-dipole, and $\pi$-$\pi$) by doping the air flow with one or more substances, and (4) separate the matrix and explosive molecules from the targeted surface by doping the air flow with easily collectable substances or particles.

None of the currently marketed handheld trace detection systems are intended to be used to directly detect explosives on people. They are limited not only by physical size and weight, but also by their performance in terms of, e.g. the false alarm rate. In addition, the concern of leaking radioactive material is the prohibiting factor for current trace detectors to be used directly on people; a non-radioactive IMS is one of the key elements for a successful trace detection handheld wand.

One of the technologies that will enable the realization of the handheld multi-function detection wand is an improved ion mobility spectrometer design that can be incorporated into a very compact size. Some additional requirements that are also necessary are: a rugged spectrometer, so that the handheld wand will not be too fragile for daily use; a non-radioactive ionization source, so that there would be no public safety concerns of using the handheld wand on people; an improved resolving power, so that there will not be too many false alarms that need to be addressed. The ion mobility spectrometer design that is described by U.S. patent application No. 60/766,825 may meet these requirements and will fundamentally improve IMS detection capability.

Generally a detector can be used in two states. A detector can be passive, identifying changes in environmental conditions, such as the release of hazardous airborne chemicals or can be active, searching an undisclosed object for explosive chemicals. Using a single detector, such as a metal detector, to identify a threat has become a common practice in airports and government buildings over the last 20 years. However, more recently multiple detectors have been utilized to screen passengers or baggage for multiple threats since criminal activity (terrorists) has become a greater concern. Portal/examination stations for detecting a plurality of threats/agents are documented in the patent art; a handheld multi-function detection wand is first time described in this invention.

Accordingly, a need remains for a handheld multiple detector wand for searching multiple threats in close proximity to the targeted area that is suitable to collect residues of explosives and other chemicals more effectively than the portal/examination stations and performs an exhaustive search for multiple threats saving valuable time and effort when detection portal/examination stations are not available due to space constraints.

The handheld multi-function detection wand is an apparatus that can detect more than one different threat in a compact unit by conducting a human body search. This device does not just have multiple detectors in order to identify and confirm the same single threat, instead the device performs an exhaustive search for multiple threats saving valuable time and effort. For example, a person can be searched for guns (metal objects) and explosives (e.g. TNT) at the same time with a multi-function detection wand that has a chemical detector and a metal detector together in one apparatus. More detectors could also be added such as an active circuit detector along with the metal and chemical detector to further identify and active bomb device on the same person.

The handheld multi-function detection wand can also be combined not only with a metal detector, but with a charge and proximity detector, active circuit detector, electromagnetic field detector, a radiation detector, a biological warfare agent detector, a radar detector, an x-ray detector or a remote detector that directly analyzes samples on a targeted surface such as a optical spectroscopy based detector. Any combination of these or other detectors not mentioned above for identifying a threat can be combined with the wand for chemical screening. These detecting devices can be incorporated into the wand solely or in a combination. These additional detecting devices can also be interchangeable modules within the compact size of the wand so that the handheld multi-function wand can be custom tailored to a particular application.

BRIEF DESCRIPTION OF THE DRAWINGS

The foregoing and other aspects, embodiments, and features of the inventions can be more fully understood from the following description in conjunction with the accompanying drawings. In the drawings like reference characters generally refer to like features and structural elements throughout the various figures. The drawings are not necessarily to scale, emphasis instead being placed upon illustrating the principles of the inventions.

FIG. 2B shows a cross section of the lower chamber with impinging airflows, the outer return airflows, and the center return airflow.

FIG. 6A schematically shows the handheld detection interrogating apparatus with docking station/charger. FIG. 6B schematically shows the difference between the detection and sampling apparatus.

FIG. 14A-D schematically shows lessening the effects of electrostatics by adding a doping substance into the sheet-like impinging airflow.

DETAILED DESCRIPTION OF VARIOUS EMBODIMENTS

In a broad sense, this invention can be viewed as a dynamic inspection method and means for conducting a comprehensive search of selectees or objects whereby the sampling of a human body or objects occurs using an interrogating apparatus in a non-contacting sweeping motion whereby one or more sweeps are performed for a targeted surface area.

In a variety of embodiments, the dynamic inspection method and interrogating apparatus may be a non-contact multi-function interrogating apparatus for detecting a plurality of threats. It should be noted that "threats" as used herein below may be, but is not limited to, chemicals, biologicals, illicit drugs, weapons, explosives, radioactive materials, or other contraband objects/substances. In addition, it should be noted that "a different threat" as used herein below may be, but is not limited to, a different component of the first threat and/or an independent threat from the first threat. For example, a pipe bomb's explosive chemical content or chemical residues would be referred as the first threat and the metal pipe in which the explosive chemical is contained could be referred as a different threat, since the metal pipe is a different component of the first threat. A non-limiting example of different threat may also be an independent threat from the first threat, such as, a metal knife along with an explosive chemical particle from a pipe bomb.

Unless otherwise specified in this document the term "jet array" is intended to mean a series discrete openings or continuous openings, such as but not limited to a series of small holes or long narrow slit that is suitable to regulate fluids into jet like motion.

Unless otherwise specified in this document the term "particle" is intended to mean chemical and/or biological molecules that are; vapor, droplets, an aerosol, liquid, solid, or any other mobile medium in which specific molecules of interest may be transported in air.

Unless otherwise specified in this document the term "ion mobility based detector" is intended to mean any device that separates ions based on their ion mobilities or mobility differences under the same or different physical and chemical conditions and detecting ions after the separation process.

Figure 1:
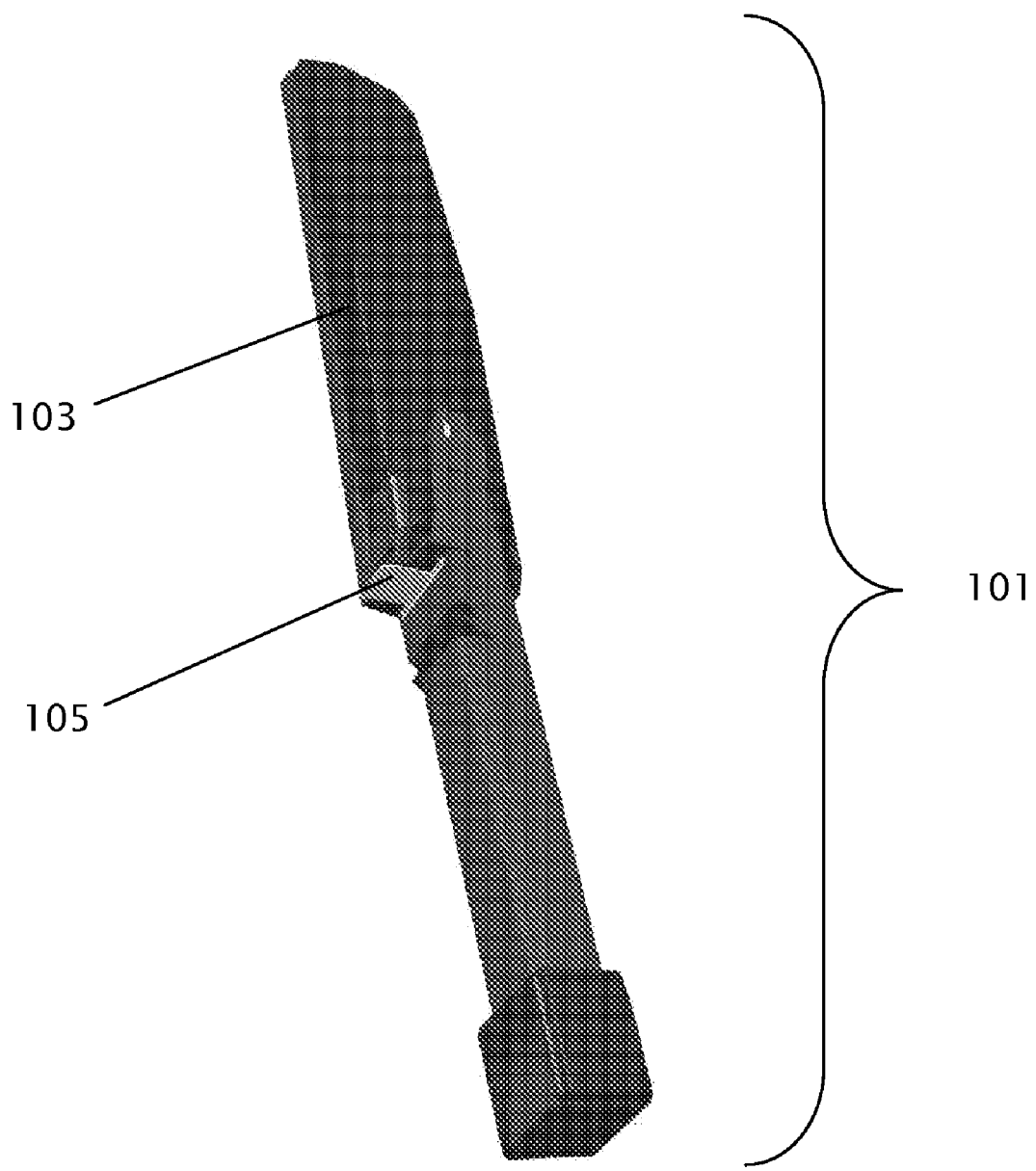
FIG. 1 is a conceptual drawing of the handheld sampling interrogating apparatus.
Figure 2A:
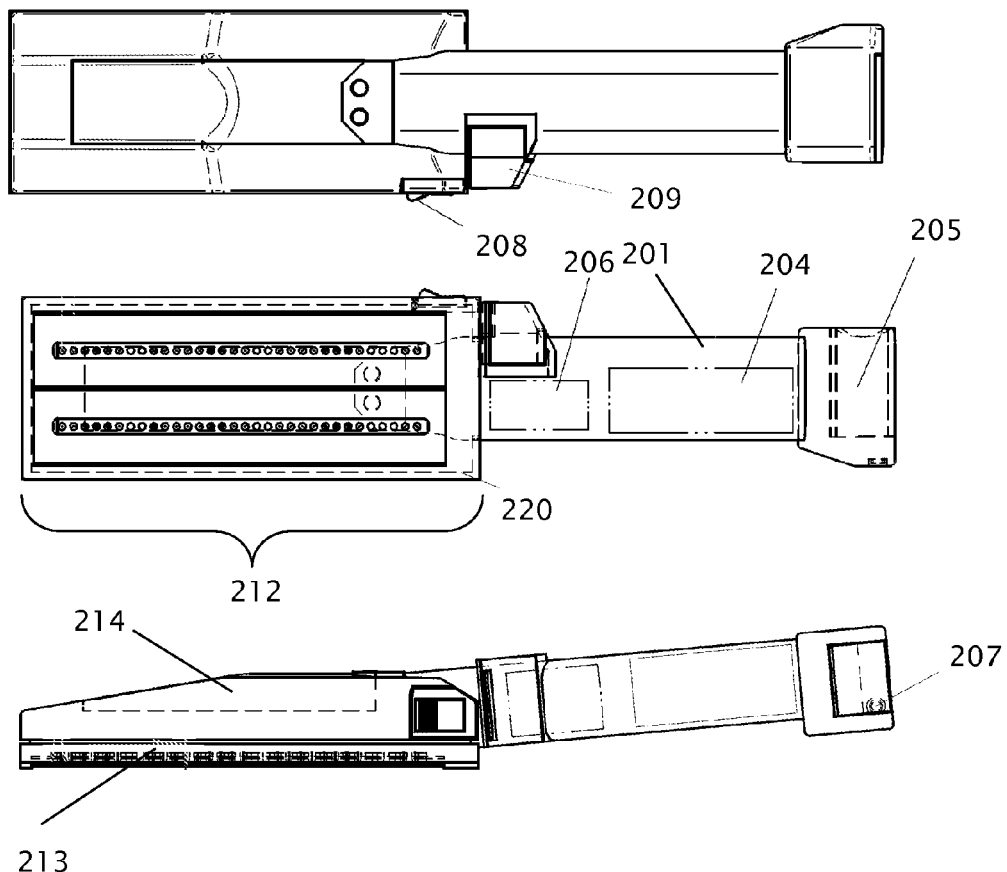
FIGS. 2A and 2B schematically shows a general design of the handheld multi-function interrogating apparatus that is compatible with current trace detectors.
Figure 2B:
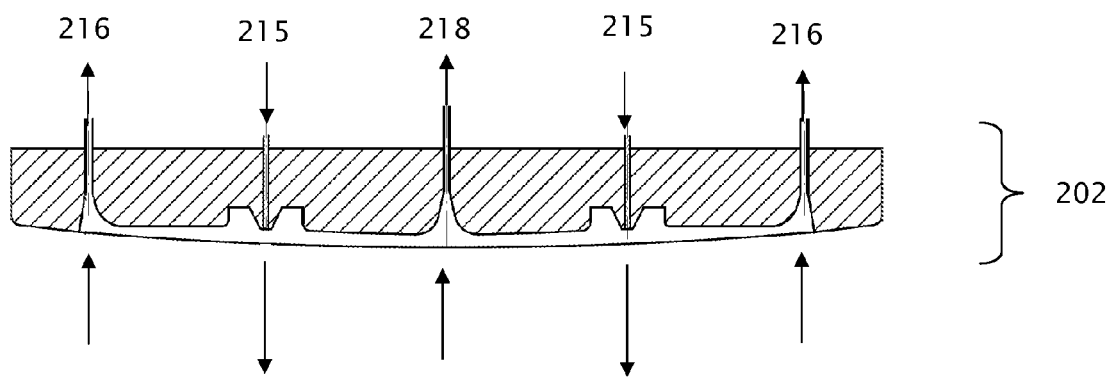
Figure 3:
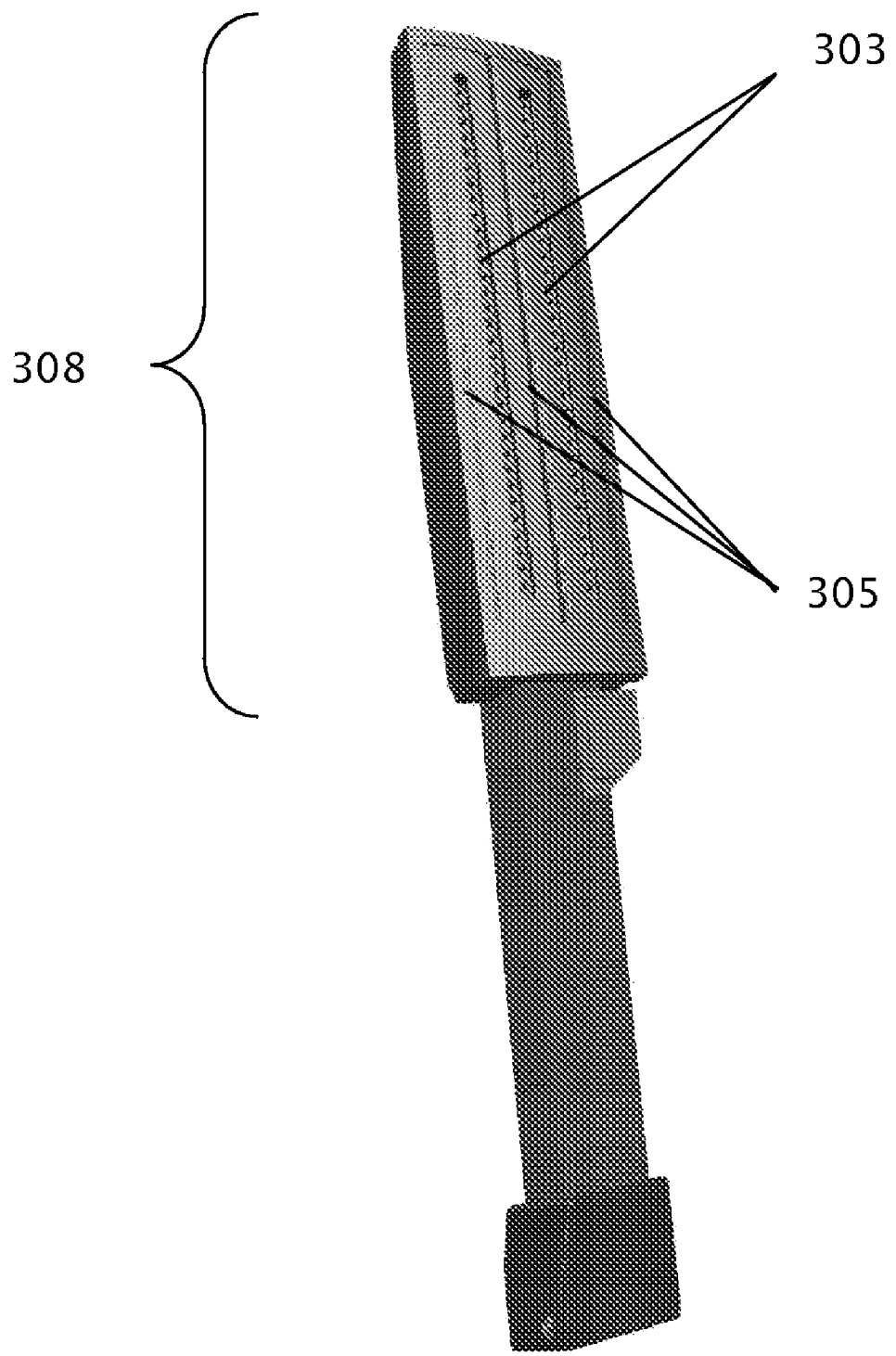
FIG. 3 schematically shows the air jet array and sample collection slits in the front sampling region of the handheld interrogating apparatus.
Figures 10A, 10B:
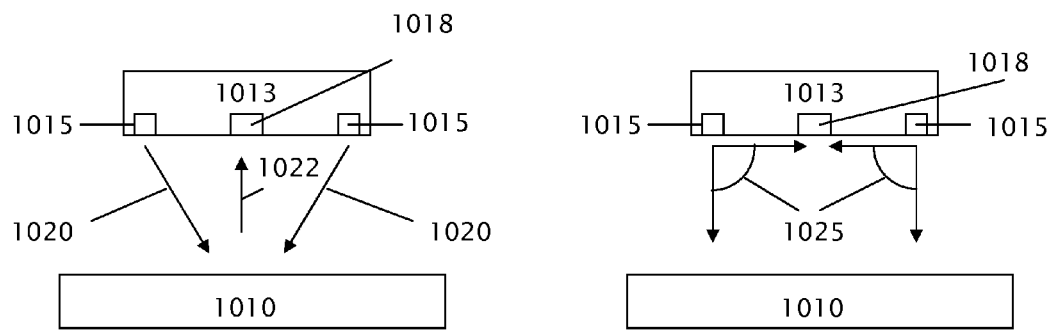
FIG. 10A schematically shows the interrogating apparatus impinging air flow and return flow.
FIG. 10B schematically shows the angle of impinging air flow.
Figure 10C:
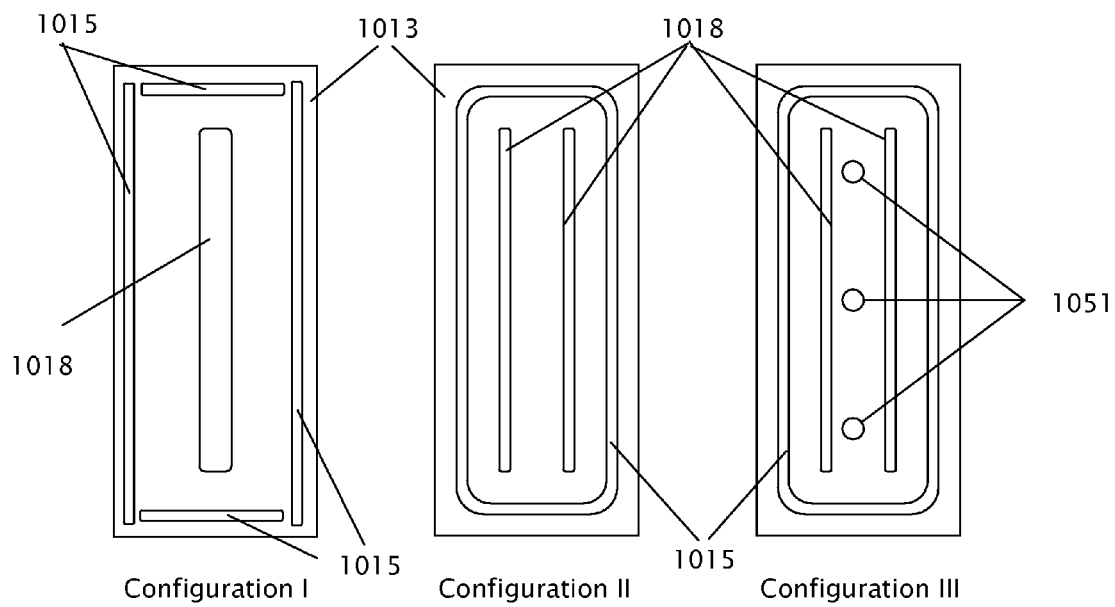
FIG. 10C schematically shows possible air flow configurations.

Unlike conventional prior art handheld chemical detectors, the interrogating apparatus (sampling and/or detection) design is for rapidly and effectively screening particles on a given targeted surface. It maximizes the exposed surface area between the interrogating apparatus and the targeted surface as prior art handheld detectors are commonly referred as sniffers that only sample chemicals from a narrow nozzle-like inlet. The sniffer design is not suitable for fast screening large areas, such as the human body. On the contrary, the interrogating apparatus described in this invention, uses the largest surface area for sample stimulation and collection on the targeted surface area by moving the interrogating apparatus in a sweeping motion. Simultaneously, in the same sweeping motion, other contrabands, such as weapons, can also be inspected. In a variety of embodiments, FIG. 1 is the conceptual schematic of the interrogating apparatus 101 as a handheld wand with a particle sampling component, a housing for multiple detectors 103 and a sample/preconcentrating filter 105. The interrogating apparatus will have a very similar shape as the commercial metal detection wands. FIG. 2A shows the engineering sketch of the device. There are three sections: (1) a handle 201 and a power source 204, (2) a middle section chamber adjoining the handle that encloses the pump or pumps 206, electronics, on-off switch 208, a temperature controller, a sample collector, and a locking and dispensing mechanism 209 for the sample collector, (3) the front sampling region 212 consisting of an upper and lower chamber that is parallel to the handle, whereby the upper chamber 214 encloses impinging and collecting airflow lines and the lower chamber consists of jets and intake holes. Also shown is a onboard battery charger 205 with a connection port 207. FIG. 2B shows the cross section 202 of the lower chamber with the impinging airflows 215, the outer return airflows 216 and the center return air flow 218. FIG. 3 provides a detailed view showing the air jet array 303 and sample collection slits 305 in the front sampling region 308 of the handheld sampling wand. A general representation as shown in FIG. 10A-C of alternative sampling port designs which can be used are; having a plurality of facing air jet arrays located around the periphery of the lower chamber of the front sampling region and a plurality of intake holes are located inside of the air jet arrays whereby a impacting sheet-like airflow is administered to a targeted surface. The jets in the arrays may be designed by having different sizes to balance the pressure and release of particles at different distances from the handheld wand.

A modularized design philosophy will be applied to the sampling handheld wand configuration. Both impinging ports 303 and sample collection slits 305 (as shown in FIG. 3) are connected to the air flow manifold at the front sampling region 308. The manifold serves as the interface between the air pump and sampling ports. When an application requires it, the front sampling region containing the lower chamber consisting of jets and intake holes may be exchanged for different sizes and shapes of air jets and intake holes. The components beyond the manifold interface could be swapped with another component that has different arrangement of sampling and collection ports. An application may require that the impinging and sampling flow have a different balance. For example, if the wand is to collect samples in a confined area, such as inside of a jacket, impinging flow pressure may be increase to reach far corners for the best result, in this case, the front portion of the wand may be replaced in situ.

In a variety of embodiments, FIG. 10A-C shows the configuration of air jet ports 1015 and intake ports 1018 are such that the air jet ports that dislodge chemical vapors and/or particles from targeted surface 1010 are on the outer region of the front sampling region and the intake (vacuum) ports are located on the interior region of the front sampling region shown in FIG. 10C. The chemical vapors and/or particles that are dislodged by an impinging air flow 1020 are suctioned with a return air flow 1022 into the intake port 1018 in the center region of the sampling wand 1013 as a closed loop air current. The air jet ports 1015 and the intake port(s) administer the sheet-like impinging air flow 1020 and the return air flow 1022. The critical angle 1025 at which the impinging air flow 1020 is impinging the targeted surface 1010 are between substantially perpendicular to substantially parallel toward the targeted surface 1010 shown in FIG. 10B. There can be many different configurations where the facing air jet arrays are located on the outer region of the wand and the intake ports are on the interior region. The sheet-like impinging air flow 1020 can be administered from a long slit or an array of small individual opening ports, whereby a uniform surface area is completely blanketed. Air jets ports 1015 can be configured with a single slit as shown in FIG. 10 or a plurality of the slits or array of single air jets cooperating in a fashion that could result in the same sheet-like impinging air flow 1020. The air jet ports 1015 do not necessary completely surround the front sampling region. As one dimension is significant greater than the other, the jets may only be arranged along the longer dimension; as shown in FIG. 10C configuration I, the top and bottom jet slit may be removed if it does not reduce the sample collection efficiency. In a variety of alternative embodiments, FIG. 10C depicts three possible configurations I-III, but the handheld wand's configurations are not limited to these examples. Configuration I has a single zone 1018 for the intake ports whereas configuration II has two zones 1018 for the intake ports. In configuration III, the intake ports are accompanied with pulsing jet ports 1051 that are all contained inside of the continuous flow jet ports on the outside of the front sampling region. The pulsing jet ports generate jet like air pulses that directly impinges on the targeted surface 1010 to assist in dislodging the chemicals from the surface. For all of the possible configurations the air jets (from ports 1015) located on the outer region of the front sampling region may be a continuous flow or a pulsing air flow.

For collecting a sample from a human body, the temperature and pressure of the impinging flow will be carefully balanced and controlled. In this design, a safety mechanism will be built in to control the electronics. The flow will automatically shut off when the temperature is over the preset limit. The sample collection flow path will be built with chemical resistive material, e.g. Teflon, so that sample loss in the flow path will be minimized. With the consideration that the metal and trace detector will be combined in the same handheld wand suitable materials will be incorporated into the design. For example non-metal materials will be used for the entire front portion of the handheld wand when a metal detector is combined in the handheld wand. As shown in FIG. 2A the metal detector coil 220 can be incorporated into the front sampling region 212 of the handheld multi-function interrogating apparatus.

A non-limiting example of a sampling event involves searching the selectee from a distance less than a half inch away from the targeted surface with the handheld wand. A constant air flow is delivered to the impinging ports. The temperature of this flow is controlled at slightly higher than human body temperature, e.g. 40-45° C. As the impinging flow on the outer layer of the clothing occurs, there are three simultaneous effects that help in collecting residue explosives: a) the relatively high speed flow from the impinging jets could release particles that are attached to the clothing, these loose particle can subsequently be pumped into the suction slits; b) the relative higher temperature could evaporate some of the explosives into the gas phase, for example, the RDX vapor pressure increase from 6.0×10−3 ppb to 0.1 ppb when temperature change from 25 to 43° C.; the vapor of explosive will be pumped toward the preconcentrator and trapped on this media; c) as the higher pressure and temperature air penetrate through the fabric, it may cause a local high pressure inside the cloth, some portion of air from inside the clothing could be collected into the adjacent suction slits. The final sample releasing/collecting efficacy is the result from these three effects.

Figure 4:
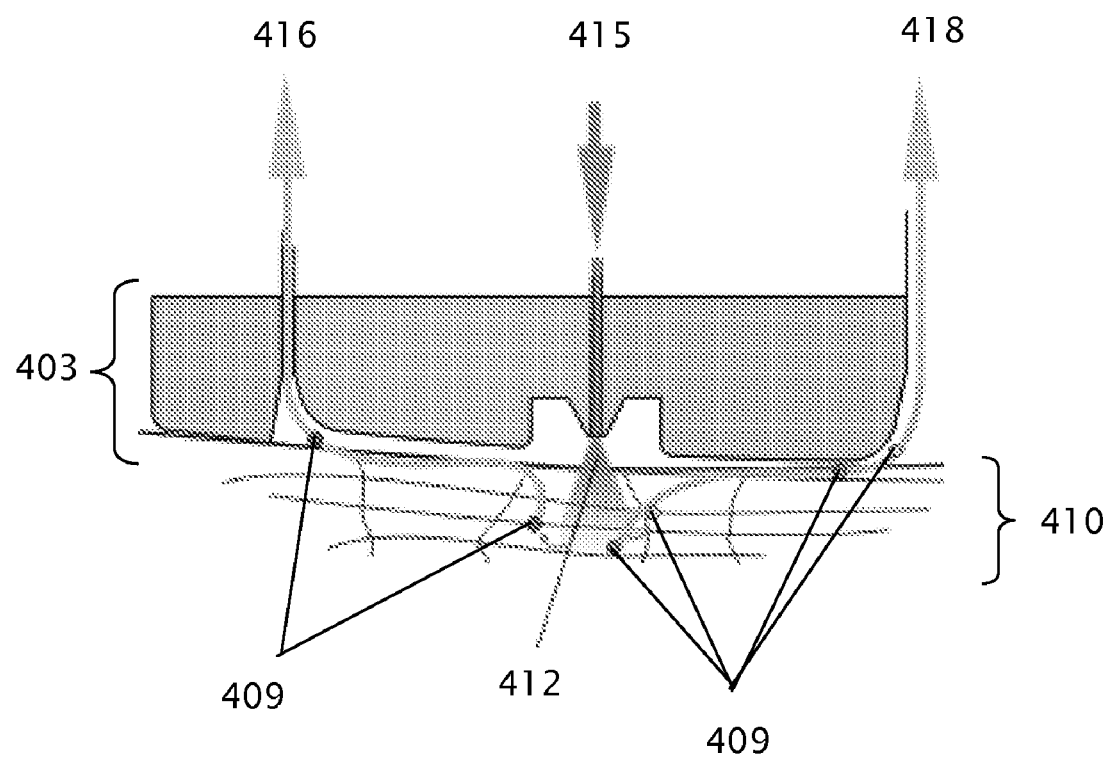
FIG. 4 schematically shows half of the cross sectional view of the lower chamber sampling particles from a targeted surface with an airflow.

FIG. 4 illustrates the above discussed sampling mechanism. The cross section view 403 represents half of the sampling handheld wand; the entire cross section 202 of this wand is shown in FIG. 2B. The impinging air flow 415, and the return (collection) flow 416, 418 is shown with the particles 409 in the air current. When the handheld wand is applied against clothing 410, the fabric can be described as in a "wave" shape, where the high point of the "wave" is created by the suction ports caused by the local low pressure; the low of the "wave" is create by the impinging flow caused by the local high pressure air 412. As the handheld wand is moved by the screener, the "wave" moves with it. During this process, available explosive particles and/or vapors are collected onto the sample collector of the handheld wand.

Figure 11A:
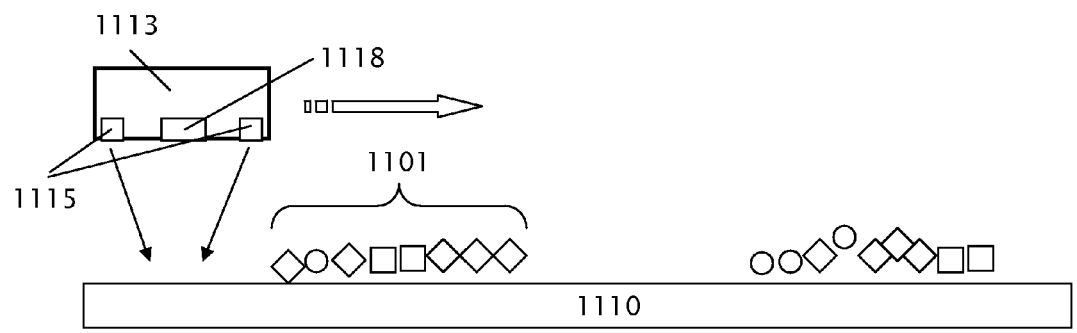
FIG. 11A-C schematically shows the dynamic inspection method, moving an interrogating apparatus in a non-contacting sweeping motion for vapor and/or particle collection.
Figure 11B:
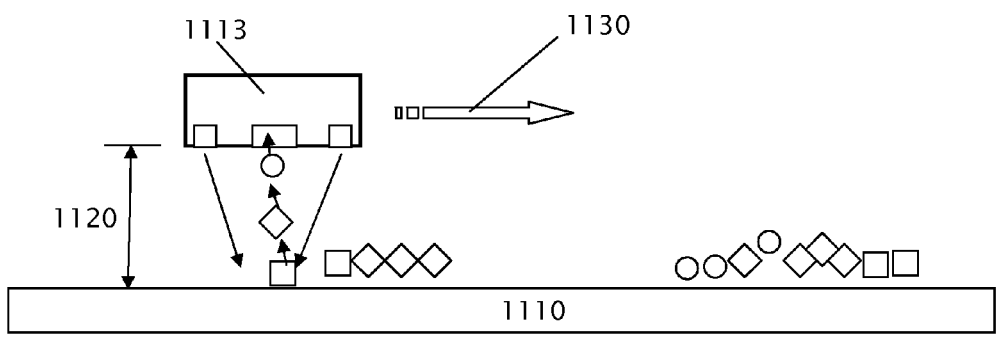
Figure 11C:
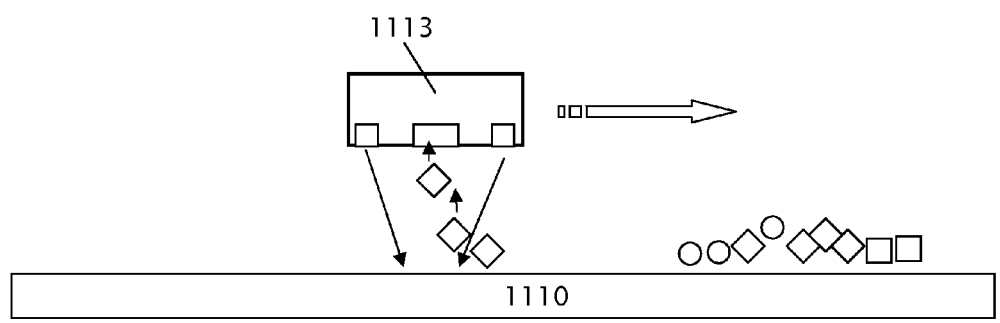

In a variety of embodiments, the dynamic inspection method shown in FIG. 11A-C of sampling a human body comprises, moving the handheld wand 1113 in a sweeping motion collecting any chemical vapor or particles 1101 that may be on a persons clothing or skin 1110. The sweeping motion is similar to using a brush to comb a person's hair, although different in that the handheld wand does not contact the surface. Instead, the handheld wand 1113 uses the impinging jets 1115 to dislodge the chemical vapors and/or particles from the clothing or skin 1110 whereby the intake port 1118 collects them. The handheld wand 1113 will not contact the clothing or skin 1110 of the person but instead will sample at a distance, e.g. ½ inch away from the clothing or skin 1120, preferably between not contacting the person and 2 inches away from the person's clothing or skin. The wand could be used at any distance in which the impinging air jets can dislodge the chemical vapors and/or particles. The handheld wand is configured such that the impinging jets 1115 and sufficient air flow rate are used to assure that movement of the dislodged particles are significantly faster compared to the sweep motion during sampling, thus the speed of the sweep motion during sampling does not affect the motion of the dislodged vapor and/or particles in the return flow. In a sampling event, the handheld wand is used to sweep a human body dislodging chemical vapor or particles 1101 that are located in the path of handheld wand's motion and subsequently collects these vapors or particles on a sample collector. The sample collector which contains the vapor or particle is either manually transferred to a detector, or is arranged directly in fluid communicating with an onboard detector to desorb and detect the vapors and/or particles from the sample collector. The above disclosed sampling method can also be applied to other surfaces that are not on a human body. Such a surface may include but not limited to, a handle of the suitcase, interior surface of a suitcase, computer keyboard, packaging boxes, etc. The disclosed sampling method can also be an automated machine controlled sweeping that could satisfy the above described sampling conditions.

The sampling/preconcentrating filter is one of the key elements of building a successful trace sampling wand. The particle sizes of explosive residues are in the range of submicron to several hundred microns. Knowledge learned from the trace detection portal system is that larger explosive particles can be more effectively collected. In addition, the large particles represent a major portion of available samples. Therefore, the preconcentrating filter will be chosen to collect particles from several to tens of microns in size. This approach can practically reduce the load of sampling pump, thus a smaller sampling pump could be used.

In addition, the sample desorption efficiency will also be considered when selecting a filter for the sample collector. In commercial trace detection systems, the thermal desorber does provide sufficient heat, fast enough to evaporate the explosives on the sample collector all at once. Although the heat transfer between the sample collector and desorber surface was slow. In this design, we use single or multiple layers of filter material, such as metal screens in the right opening size to preconcentrate explosives. Efficient heat transfer will result in significant sensitivity improvement compared to currently available sample collectors. If the trace sampling handheld wand had a comparable sampling efficiency as the current wiping wands, the trace sampling handheld wand can potentially be used for not only people sampling, but also on objects currently screened by the swabbing method.

For vapor sampling, the filters, such as metal screens will also be coated with a layer of affinitive material, such as modified PDMS used for SPME. Possible coating material may also include a functionalized surface, such as sol-gel. The sampling handheld wand may be made to reuse sampling materials that did not cause an alarm in the trace detection systems. For the trace detection handheld wand, the sample collector if it is necessary to preconcentrate the particles, will be reused until loss of collection efficiency occurs; the material is self cleaned during each flash heating cycle.

In the case when the multi-function handheld wand does not contain an onboard detector for analysis of sampled chemicals, a sample collector consisting of a filter material that can withstand high temperatures such as but not limited to metal, Teflon, ceramic, etc. is manually inserted into the handheld wand before sampling the human body and then when the sampling is completed, the sample collector is manually removed and inserted into a detection system for analysis. When sampling a human body for chemical vapors and/or particles, the clothing and skin that are sampled from can also contain "dirty" particles such as lint, hair, crumbs, etc. (not limited to these) that gets collected on the filter along with the desired chemical vapors and/or particles. These "dirty" particles are transferred into the detector as well when the filter's contents are desorbed for analysis. With constant use it would only take a short amount of time for the detector to accumulate a large amount of these "dirty" particles and need to be serviced to rid the detector of these "dirty" particles. These "dirty" particles can also have the desired chemical vapors and/or particles adhered to them, so removing them from the filter before detector analysis would not be prudent.

Keeping these "dirty" particles along with the chemical vapors and/or particles on the filter can be accomplished by sandwiching the contents of the collection between two surfaces such as plates, screens, filters, etc. (not limited to these). Keeping these "dirty" particles along with the sample on a filter can not only be used for the interrogating apparatus disclosed herein, but this method and concept can also be used for other devices.

Figure 12A:
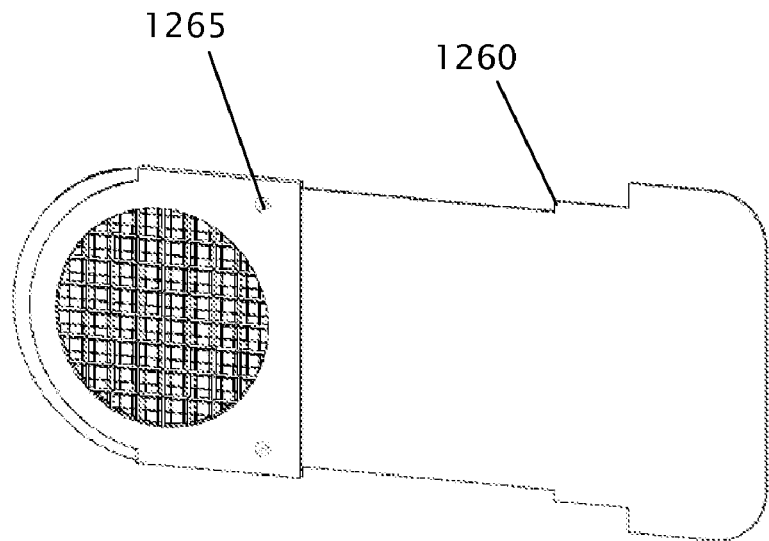
FIG. 12 schematically shows a preconcentration trap filter with movable screen.
Figure 12B:
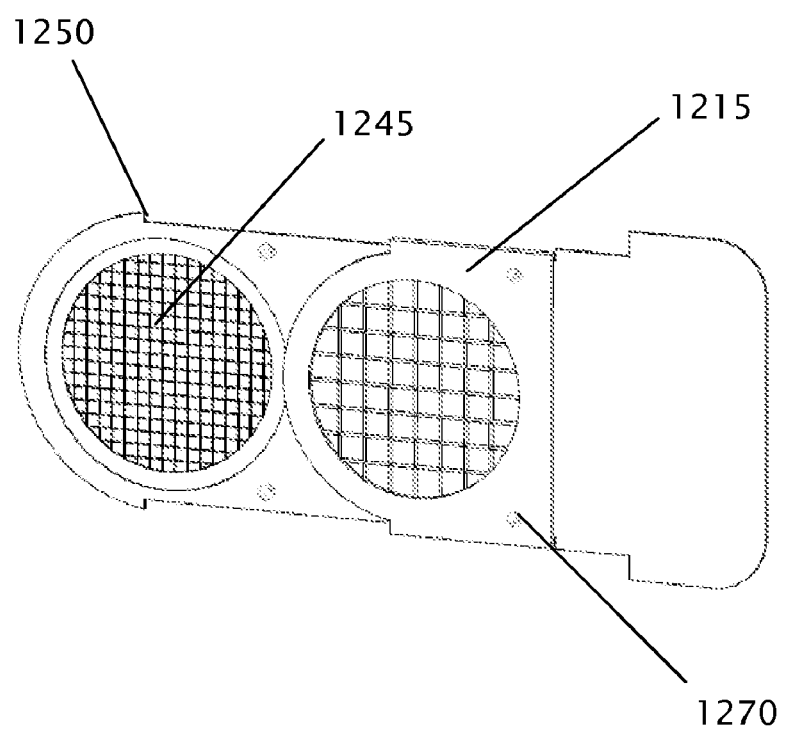

In a variety of embodiments, this sample collector comprises (a) a movable screen that can be lock at positions where the sampling material is covered or uncovered. The covered position is for transporting sample, desorbing and detecting samples from the sampling material, and the uncovered position is for collection chemical vapors and/or particles onto the sampling material; (b) a self locking mechanism that locks the movable screen in uncovered position in the handheld wand during sampling and in covered position when removed from the handheld wand through transportation and detection. In a variety of embodiments, the sample collector comprises a sampling/preconcentrating material 1245 where the chemical vapors and/or particles are trapped during the sampling of a human body and a movable screen 1215 that can be positioned so that it covers the sampling/preconcentrating material or so that it does not obstruct the sampling/preconcentrating material 1245 as shown in FIG. 12. Before using the sample collector, the moveable screen assembly 1215 covers the sampling/preconcentrating surface, FIG. 12A. When the sample collector is inserted into the handheld wand before sampling, the moveable screen assembly 1215 slides away from the sampling/preconcentrating surface 1245 so that it is unobstructed. A protruding surface in the wand catches the hole/bump 1270 and slides the moveable screen until it is stopped by a ridge in the surface 1260. Sampling takes place with an unobstructed sampling/preconcentrating surface configuration, FIG. 12B. When the sample collector is removed from the handheld wand, the moveable screen slides over the sampling/preconcentrating surface 1245 until it is stopped by a ridge in the surface 1250. With the sample collector removed from the handheld wand the sampling/preconcentrating surface is covered by the movable screen as shown in FIG. 12A and the movable screen is locked into place by having the bumps overlap 1265. The sample collector is manually inserted into the detector and the contents are desorbed with the moveable screen covering the sampling/preconcentrating surface, FIG. 12A. After analysis, and removal of the sample collector from the detector, the moveable screen can be positioned so that the remaining "dirty" particles can be wiped off the sampling/preconcentrating surface and the sample collector can be re-used in another sampling event.

In a variety of embodiments, the sample preconcentrating surface 1245 are made of multilayer diffusion bonded metal screens. Each layer of the screen may have difference opening sizes. The multilayer sample preconcentrator is intended to separate and collect particles of different size simultaneously without significantly increasing flow resistance during the sample collection process. The screens can be made of, but not limited to, stainless steel, bronze, Monel, and other metal alloys. The opening of the screen may be in the range from sub-microns to hundreds of microns.

Figure 13:
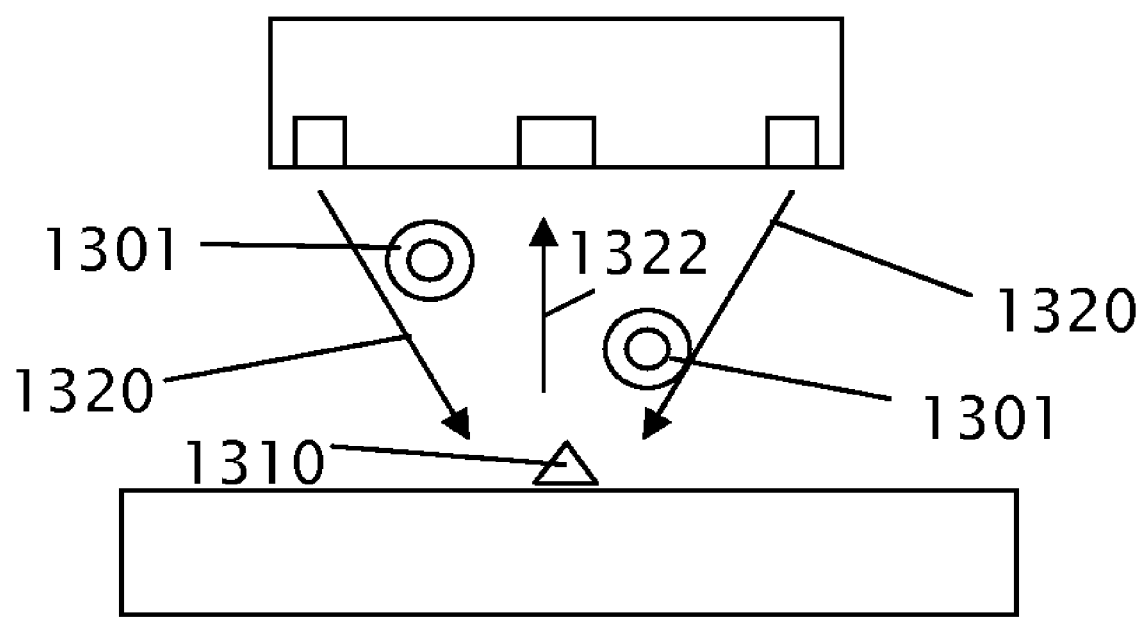
FIG. 13 schematically shows the addition of a doping substance into the airflow of the interrogating apparatus.

In addition to releasing particles with only the impinging air flow, since certain explosive materials are inherently sticky, such as C-4 (a RDX based explosive), and Deltasheet (PETN based explosive) the temperature of the air flow or the addition of a doping substance 1301 into the airflow 1320 will assist in lifting and collecting the particles of interest 1310 in the return airflow 1322 as shown in FIG. 13. As discussed below, the doping substance can be in many forms and can be added to one, a portion, any combination, or all of the airflows from the interrogating apparatus. Due to their makeup, these explosive molecules are generally greasy substances and are hydrophobic. Particles of interest to this invention which are not explosive molecules can also be hard to remove from the targeted surface and the methods and apparatus disclosed below can be used not only for explosive molecules, but for particles in general. For the purpose of describing these general methods and the apparatus, explosive molecule examples will be discussed.

As used herein, a "doping substance" is in the form of: vapor, droplets, an aerosol, liquid, organic solvent, solid, resin bead/s, polystyrene matrix, atom, molecule, compound, metal, alloy, or any other mobile medium in which can be transported in an airflow. The use of a doping substance to assist particle release from a targeted surface can not only be used for the interrogating apparatus disclosed herein, but this method and concept can also be used for other devices.

It is also to be considered that the handheld wand can be used to sample objects besides people, in this case more flexible parameters could be used to release explosives from the surface. For example, the temperature of the impinging air can be significant increased to evaporate the explosive in to the gas phase. The impinging air pressure and different sizes of the nozzles in the impinging jet array may be optimized to achieve maximal particle removal and collection efficiency.

In a sampling event electrostatics (static electricity) can affect the ability for the non-contact interrogation apparatus to collect the explosive particles 1402 from the targeted surface 1401 as shown in FIGS. 14A-C. For example, when two non-conducting materials 1402 and 1401 come into contact with each other, an adhesion is formed between the two materials, FIG. 14A. Depending on the properties of the materials, the adhering force between two materials may be caused by a charge imbalance. In order to neutralize the charge imbalance and lessen the adhesion between materials, a low-resistance path for electron flow is provided. Water 1410 can be added as a doping substance to the sheet-like impinging air flow 1420 which lightly mists the targeted surface neutralizing the charge imbalance shown in FIG. 14B. Therefore the adhesion between materials is lessened as shown in FIG. 14C and the explosive particle 1402 is collected more effectively. In addition to water, plasma (ionized air) can be used to remove static electricity, dust particles, and waxes. Ions and free electrons can be added as a doping substance to the sheet-like impinging air flow 1420 to neutralize the charge imbalance between materials by bombarding them with a charged species. The bombardment with ions and/or free electrons 1415 can dislodge explosive particles 1402 from the targeted surface 1401 and then be collected in the return air flow 1422 by way of the closed loop air current as shown in FIG. 14D.

Figure 15A:
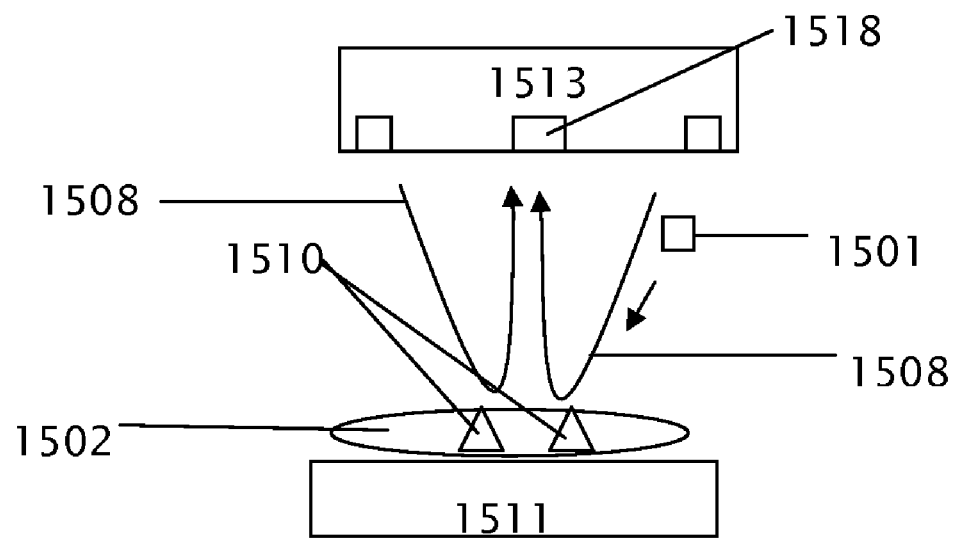
FIG. 15A-B schematically shows the removal and collection by way of a closed loop air current of explosive particles from matrix by selective interaction with the doping substance.
Figure 15B:
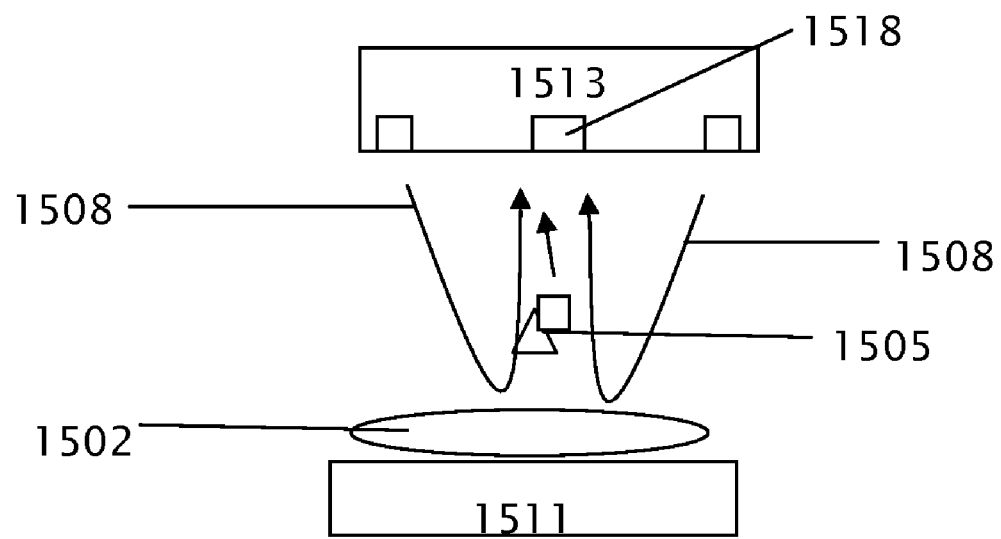

Since explosive particles have molecular functionality which is different from the matrix that is adhered to the targeted surface, a doping substance which selectively interacts with the explosive's particles functionality can help remove the explosive particle from the matrix as shown in FIG. 15A-B. A doping substance 1501 can be added to the sheet-like impinging air flow which bombards the targeted surface 1511 and hits the entrained explosive particle 1510 in the matrix 1502 whereby the explosive particle 1510 attaches to the doping substance 1501 forming a complex 1505 which is removed from the matrix 1502 by bouncing off the targeted surface 1511 into the intake port 1518 of the interrogation apparatus 1513 by way of the closed loop air current 1508 as shown in FIGS. 15A-B. The attachment of the explosive particle to the doping substance is accomplished by utilizing intermolecular interactions that are exclusive to the explosive molecule such as ionic interaction, hydrogen bonding, dipole-dipole, and π-π. An example of using hydrogen bonding as the intermolecular interaction is discussed below.

Figure 16A:
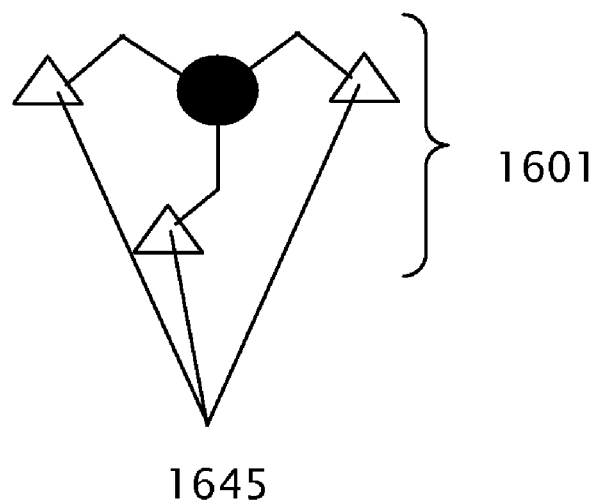
FIG. 16A-B schematically shows an alcohol group as one of the many reactive sites on a resin bead that binds to the nitro group functionalities (via hydrogen bonding) that are commonly found in explosive particles.
Figure 16B:
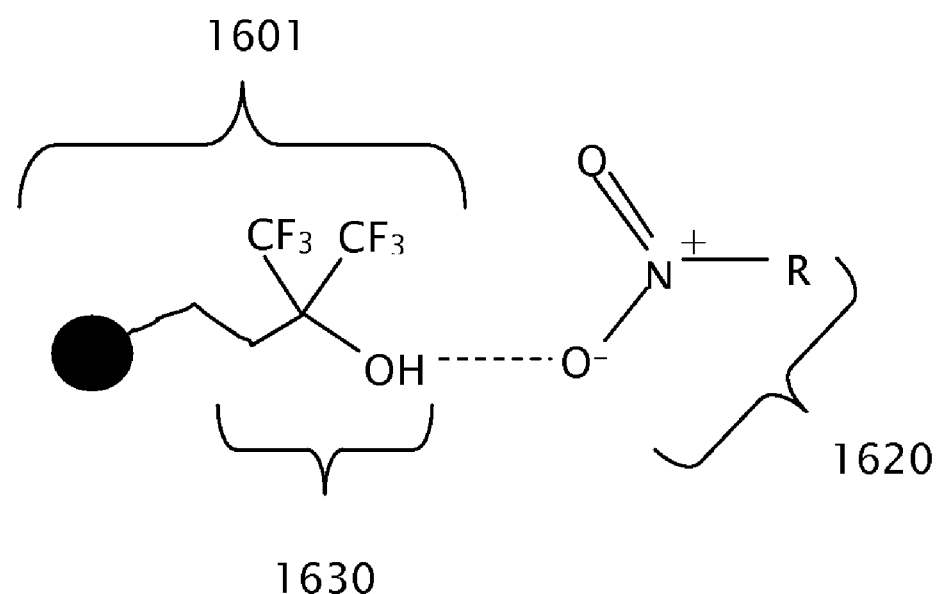

Many explosive molecules have a nitro-group functionality, such as RDX, which has three nitro functional groups. An interaction that can have some selectivity and also be reversible is hydrogen bonding. Hydrogen bonding occurs when a hydrogen atom is covalently bonded to a small highly electronegative atom such as nitrogen, oxygen, or fluorine. The hydrogen atom has a partial positive charge and can interact with another highly electronegative atom in the explosive molecule. The Oxygen atoms in the nitro groups can participate in hydrogen bonding by being the hydrogen bond acceptor. The hydrogen bond donor could come from a number of sources; alcohols, phenols, thiols, amines, etc. For example, a doping substance such as a resin bead 1601 can have a plurality of reactive sites 1645 shown in FIG. 16A. It has been shown that strongly acidic polymers, such as SXFA-[poly(1-(4-hydroxy-4-trifluoromethyl-5,5,5-trifluoro)pent-1-enyl)methylsiloxane], bind to the basic lone pairs of the nitro groups. The strongly electron withdrawing nature of the two adjacent trifluoromethyl groups to the alcohol group increase the hydrogen bond acidity and therefore illustrate a stronger interaction. This alcohol group (hexafluoroisopropanol) 1630 can be chemically linked through covalent bond to a bead-like carrier, e.g. polystyrene matrix forming resin beads 1601 and binds to the basic lone pairs of the nitro groups 1620 shown in FIG. 16B. In this case, resin beads 1601 are the doping substance that is added to the sheet-like impinging air flow which bombards the targeted surface.

When a large particle like doping substance, e.g. 2% cross-linked, 200-400 mesh, 2 mmol N/g resin, or other solid matrix material (e.g. Teflon) is used in the interrogating apparatus's airflow, the large particle may enter the intake port of the interrogation apparatus by way of the closed loop air current and may be deposited on the sample collector. The mesh size of the preconcentrating filter would be adjusted to collect the doping substance. For example, these large particle like doping substances are doped into the impinging airflow, interact with the explosive on the targeted surface, return via the return flow, and are trapped on the sample collector. The trapped doping substances can also collect vapor during the time they are trapped on the collector. In a variety of embodiments using resin beads as the doping substance, in addition to binding the explosive molecules by the interaction through bombardment, the free reactive sites on the deposited resin beads can interact with vapor that gets cycled through the closed loop air current, thus effectively collecting vapor on the sample collector.

In a broad sense, any doping substance which can be trapped on the preconcentrating filter has the ability to collect vapor in the return flow of the closed loop air current. A doping substance can have a layer of affinitive material, such as modified PDMS used for SPME or a functionalized surface, such as sol-gel that can collect vapor.

Figure 17A:
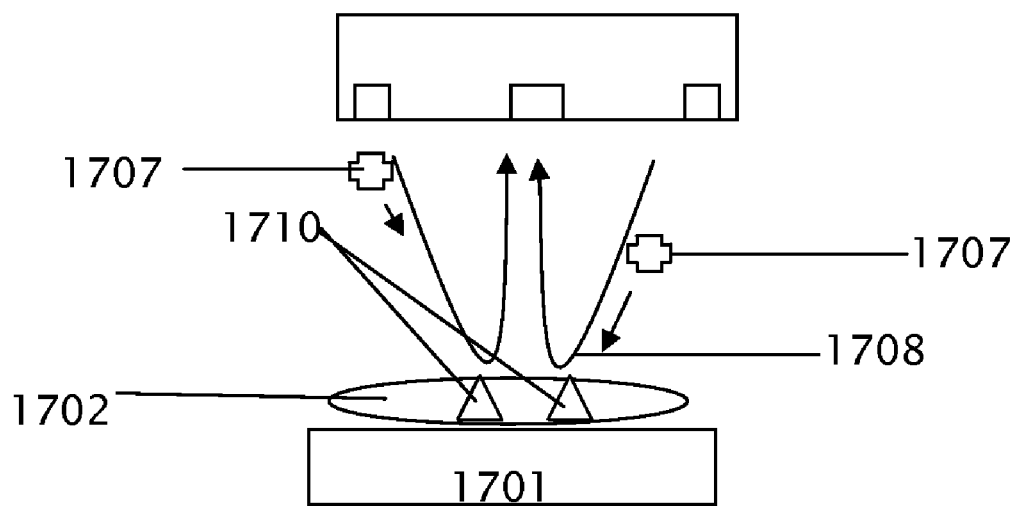
FIGS. 17A-B schematically shows a liquid phase doping substance that can remove the matrix and explosive particle together and collect them in the interrogating apparatus by way of the closed loop air current.
Figure 17B:
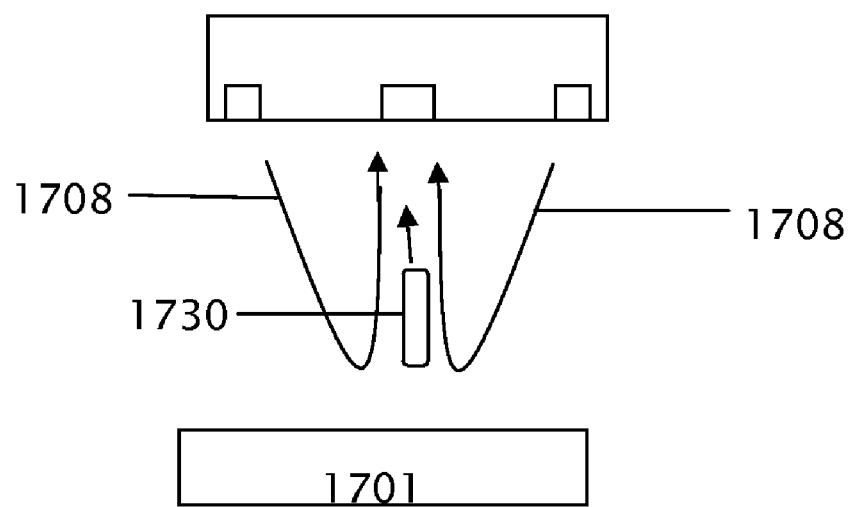

Another use of a doping substance which is added into the airflow to assist in lifting and collecting the chemicals of interest is a doping substance that may remove both the matrix and explosive molecules together. In order to separate the matrix 1702 and explosive molecules 1710 from the targeted surface 1701, such as a fabric (found on luggage and clothing), a doping substance 1707 such as perchoroethylene, cyclic silicone decamethylcyclopentasiloxane, and liquid $CO_2$, but not limited to these chemicals can be added to the air flow of the interrogating apparatus as shown in FIGS. 17A-B.

This process is effectively the same as dry cleaning clothing and textiles using an organic solvent other than water. The matrix 1702 and explosive molecules 1710 are effectively removed from the targeted surface by solvation into the doping substance 1707 when they come in contact forming a mixture 1730 that can be extracted by way of the closed loop air current 1708.

Figure 18A:
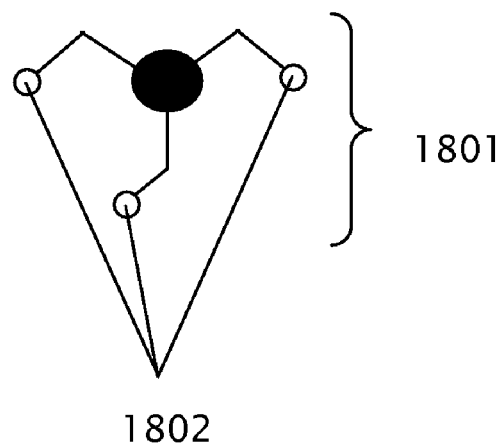
FIGS. 18A-B schematically shows a solid phase doping substance that can interact with the matrix and explosive particle together and collect them in the interrogating apparatus by way of the closed loop air current.
Figure 18B:
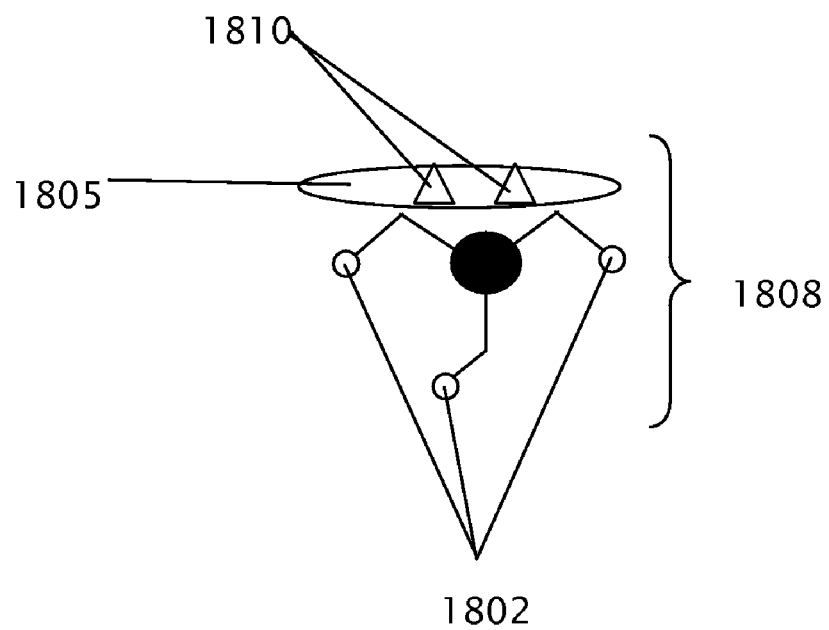

In addition to adding an organic solvent to remove and/or separate the matrix and explosive molecules from the targeted surface by way of solvation between liquids, a solid doping substance can be added to the air flow of the interrogating apparatus to interact with the matrix and explosive molecule as shown in FIGS. 18A-B. An example of such a doping substance are hydrophobic groups 1802, such as an alkane, alkene, benzene derivative, haloalkane, etc., that are chemically linked through a covalent bond to a peptide like carrier, e.g. polystyrene matrix forming resin beads, 1801. These resin beads are added to the sheet-like impinging air flow which bombards the targeted surface, picking up some of the matrix 1805 and explosive molecules 1810 forming a mixture 1808, and are collected into the intake port of the interrogation apparatus by way of the closed loop air current.

Figure 19A:
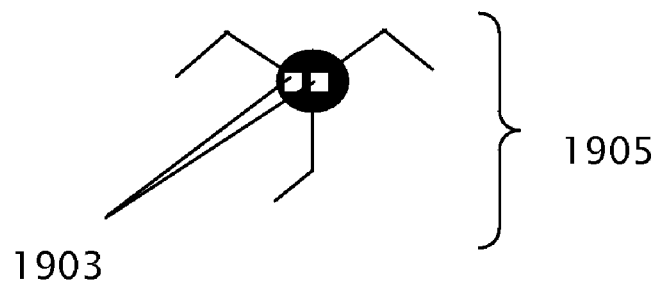
FIGS. 19A-B schematically shows a doping substance that has a magnetizable material physically admixed within, or chemically combined.
Figure 19B:
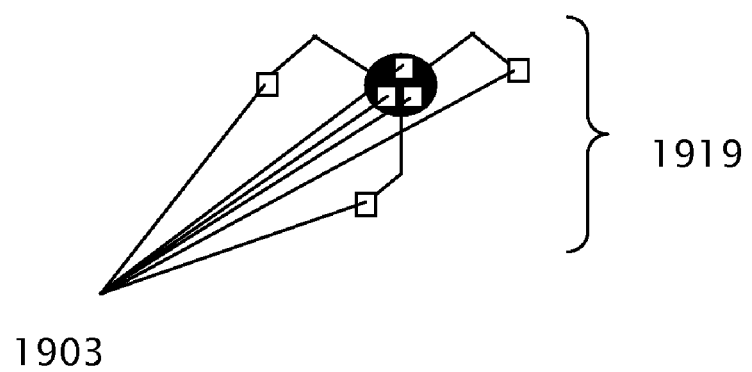

In another aspect of the invention the doping substance may contain one or more metals and/or magnetizable materials therein as shown in FIGS. 19A-B. As an example, the doping substance may be a polymer comprising a metal and/or a magnetizable material 1903, for instance, physically admixed within the polymer 1905, or chemically combined with the polymer 1919 (either internally, externally, or both). Resin beads or other solid matrix material e.g. silicon, can have a magnetic component chemically linked to a portion of the polymer matrix. For example, an iron complex linked to a portion of a Teflon bead would assist in the collection of the Teflon beads if the particle sampling component of the interrogating apparatus had the presence of a magnetic field. The applied magnetic field could be created by permanent magnets, electromagnets, or the like. Examples of metals that could be combined with the doping substance include, but are not limited to, lead, bismuth, cadmium, tin, indium, zinc, antimony, copper, silver, gold, iron, or the like.

The trace sampling wand design (size, general shape) may be used for the trace detection handheld wand based on improved IMS, however several different apparatus configurations could be built based on the sampling method including, (a) adding a suitable IMS detector onboard: as the IMS is still the most versatile trace detector available for portable applications, the device is aimed at having a trace detection handheld wand with a rugged, compact, high performance IMS inside the device; (b) The trace sampling handheld wand concept may be used with other detection methods. Besides the IMS detector, for different applications, other detection methods, such as florescent detectors, chemiluminescent detector, will also be considered; (c) combining the sampling handheld wand with multiple detectors, such as a metal detector, will have added benefits by simplifying screening operations and removing intermediate searching steps at check points.

Figure 5:
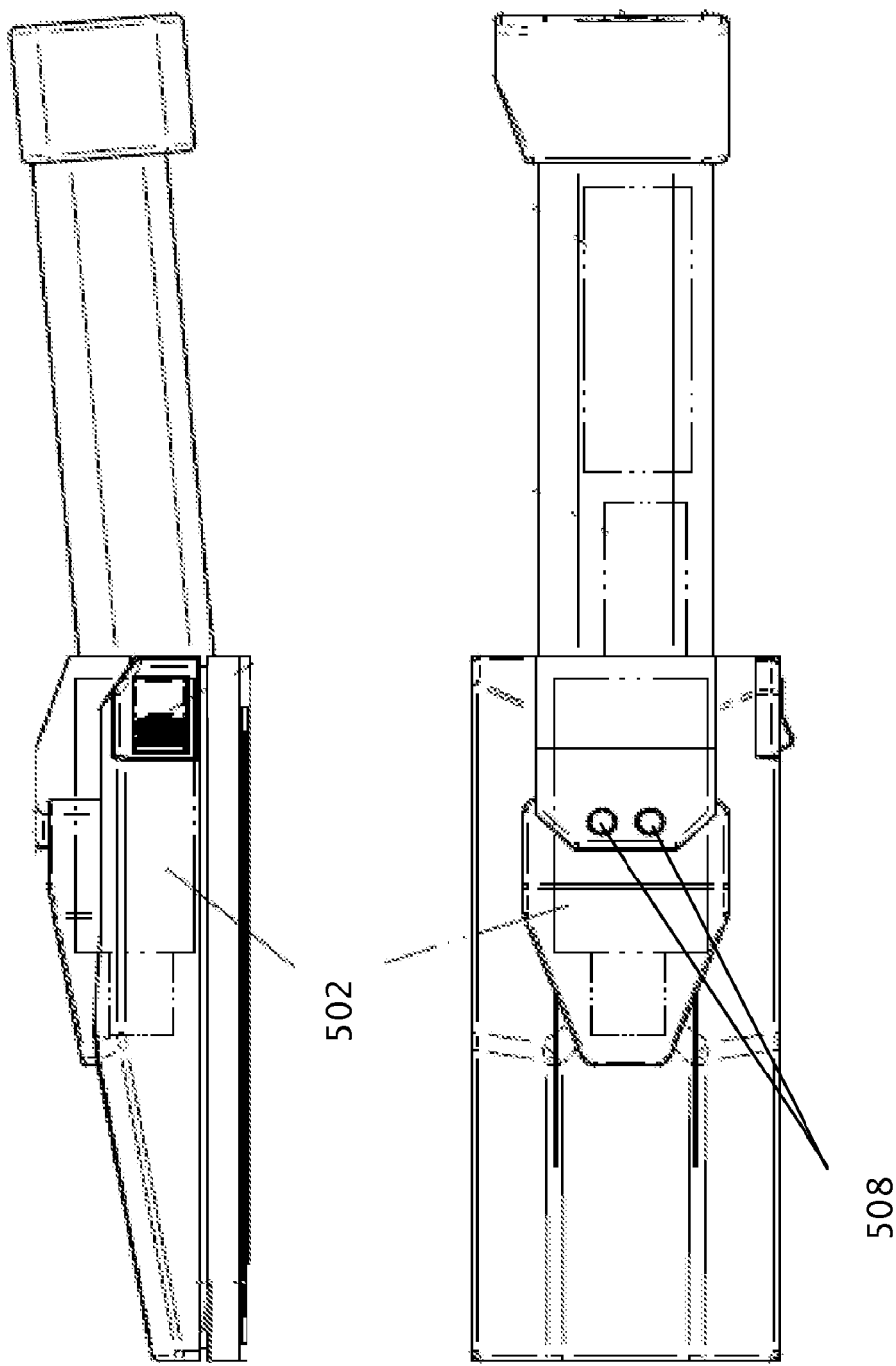
FIG. 5 is a conceptual drawing of the handheld detection interrogating apparatus.

A trace detection handheld wand can not only collect/preconcentrate explosives, but also detect them in situ. The overall system size will increase when an IMS based detector is included in the handheld wand; however, a novel IMS design that may significantly reduce the space requirement compared to conventional drift ring designs used by all commercial IMS manufactures will be utilized. As shown in FIG. 5, the height of the device will be adjusted to accommodate the detector 502. From a system design point of view, the detection handheld wand will only include basic features for sampling, preconcentrating and detecting explosives. There is no display or other user controls available on the device. However, the handheld wand can be reconfigured when it is sitting on the docking station/charger 602 (shown in FIG. 6A). FIG. 6B shows the difference between a sampling wand 606 and detection handheld wand 604. The sample trap dispenser and lock 609 are removed from the detection handheld wand 604. More electronic control components will be packed in the detection handheld wand.

The trace detection may be operated in operational modes, for example, if the search of interest is to find a specific location on the object, where the explosive or other chemicals are hidden, the handheld wand could be operated in an online detection mode, it detects the chemicals without or a minimal preconcentration time while the handheld wand is moving around the surface area. If the search of interest is to find whether an individual or object is contaminated with the targeted chemicals, the handheld wand could be operated in a batch detection mode, where it preconcentrates and detects the chemical with maximum sensitivity. As shown in FIG. 5, the detection result will be shown as "Red" or "Green" indication lights 508 besides the audible alarms; the alarm data could be sent to a remote computer or PDA via wireless communication. In a variety of embodiments, the size of the detection handheld wand is 40 L×10 W×10 H cm and weighs less than 3 lbs. The targeted size is estimated based on required sampling area, available sampling pump and anticipated detector size.

In a variety of embodiments, the handheld multi-function detection wand, with an onboard detector such as an ion mobility based detector (not limited to only this particular detector), can be operated to perform analysis of chemicals from a surface in real time, such that there is no preconcentration of chemical vapors and/or particles. During a sampling event (a scan of potential threats), the chemical vapors and/or particles are directly carried into the detector as they are being sampled into return air flow. This instrument configuration and operating method is useful for analysis of chemicals that may decompose while being thermally desorbed from the preconcentrating trap to the detector and are therefore not correctly identified. Another advantage already stated that this operation allows scanning for multiples threats simultaneously, such as detecting chemicals and metal objects, and identifying the exact location of the chemical on a subject while conducting the inspection.

Figure 9:
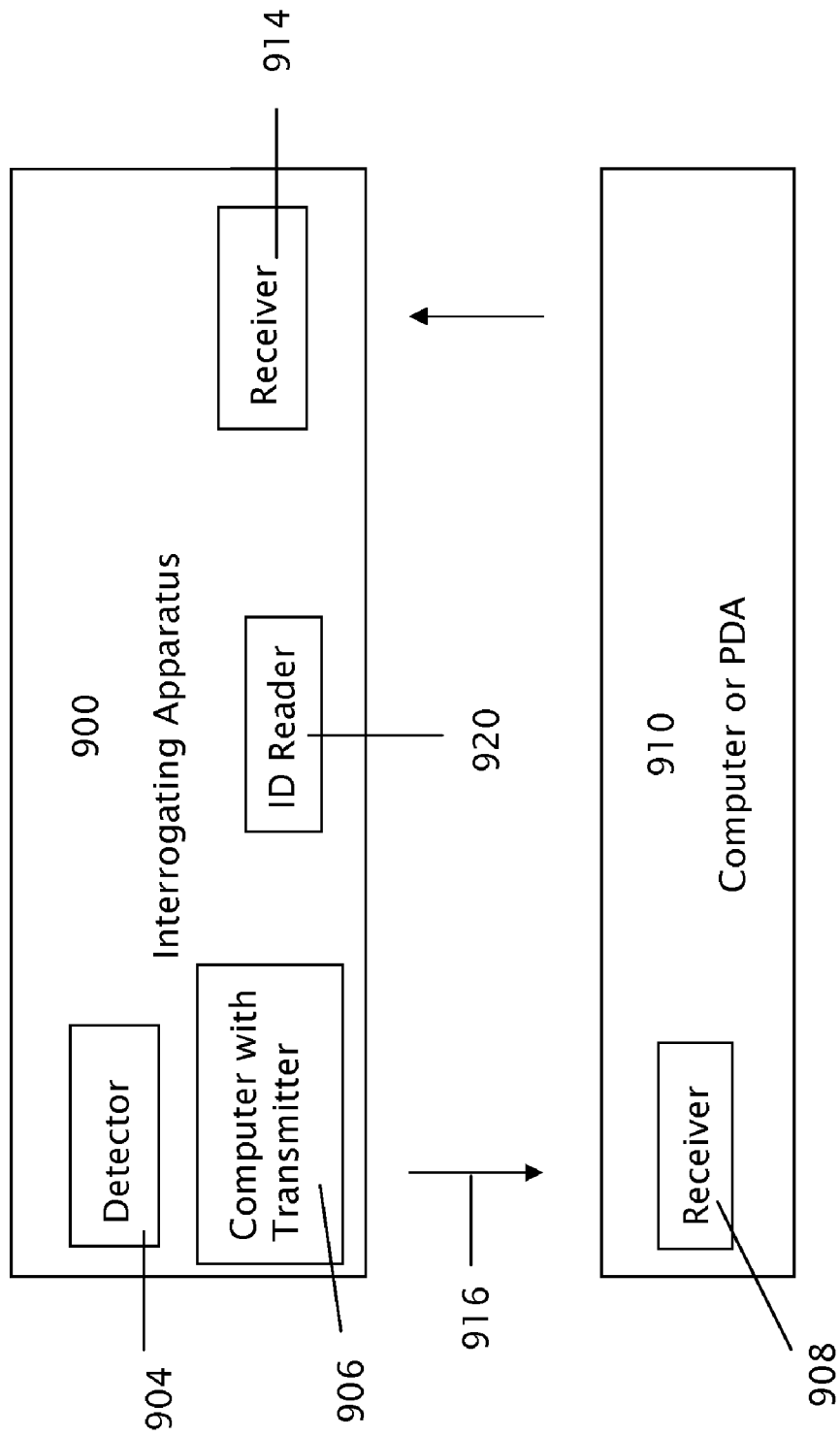
FIG. 9 shows a diagram of communication between the handheld detection interrogating apparatus and a remote PDA or computer.

Shown in FIG. 9, when the handheld multi-function detection wand (interrogating apparatus) 900 incorporates an onboard chemical detector 904 such as an ion mobility spectrometer, the samples test result can be transmitted to a computer or data terminal that connected to handheld wand. The connection can be either a wired or wireless. In case of wireless connection, such as 802.11, IR, or Bluetooth, is used, the onboard wireless transmitter 906 and send data or command to a receiver 908 housed in a computer terminal or PDA 910. The handheld multi-function detection wand 900 will also incorporate a receiver 914 whereby wireless communication from the computer terminal or PDA will be received. Wireless communications between devices can be through one of several electromagnetic communications spectrums, including radio-frequencies, microwave frequencies, ultrasound or infrared. A positive detection result would have an audible alarm from the wand 900 and computer terminal or PDA 910 as well as visual indicator lights such as a red indicator. However, communications between wand 900 and receiver 908 can also be one way, e.g., wireless data 916 from wand 900 to receiver 908; and in such an embodiment the receiver 908 preferably understands the communications protocols of data 916 to correctly interpret the data from the wand 900. Receiver 908 in this embodiment "listens" for data transmitted from wand 900. Receiver 908 thus may function as a remote receiver stationed some distance (e.g., one or tens of feet or more) from wand 900. In this embodiment the data communication between the wand 900 and receiver 910 is preferably "secure" so that only a receiver with the correct identification codes can interrogate and access data from the wand 900. A positive detection result would result in a visual, sensory (vibration), or audible alarm to the computer terminal or PDA 910 whereby the sampler and person being sampled are not aware of a positive detection, but would immediately notify a security person/s to take the appropriate actions. In this situation the person being sampled is not aware that he or she has been identified and therefore would not flee or harm the sampler in any way. The handheld wand may also include a reading device that can read and transmit the identification of the sampled subject, such reading device 920 may include but not limited to barcode reader, Radio Frequency ID (RFID) reader. Also, the wand 900 may further comprise a GPS location device incorporated into the wand so that the location of the wand 900 and alarms could be identified and allocated at any time. The data reported by the handheld wand can also be incorporated with other tests result either onboard or at remote computer using an integrated data analysis programs. Potential threats could be identify and confirmed using multiple, yet orthogonal detection methods, such as but not limited to millimeter wave, x-ray, quadrupole resonance, CT, terahertz, etc.

In a variety of embodiments of ion mobility based detector, a novel compact resistance coil ion mobility spectrometer (RC-IMS) detector for trace detection wand: The RC-IMS (U.S. Patent Application No. 60/766,825) uses helical resistive material to form constant electric fields that is used to guide ion movements in a ion mobility spectrometer. This drift tube for ion mobility spectrometer is constructed with a non-conductive frame, continuous resistance wires, an ion gate assembly, a protective tube, flow handling components, an ion detector assembly, and other components. The resistance wires are wrapped on the non-conductive frame which form coils in a round shape. The coil generates an even and continuous electric field that guide ions that drift through the ion mobility spectrometer.

The resistance wires are not only used to form an electric field, it also functions as the heating element to heat up the drift tube. The ion mobility spectrometer design controls drift tube temperature using the above mentioned coil to maintain drift gas temperature and a separate heating element is used to preheat the drift gas before entering the drift region. The drift gas is delivered directly inside the coil and pumped away from the gas exit on the protective housing. This configuration provides a robust ion mobility spectrometer that is simple to build with lower thermal mass along the ion and drift gas path, thus allowing rapid temperature changes required by some applications. In summary, the drift tube design enables an ion mobility spectrometer to be built with lower weight, lower power consumption, lower manufacturing cost, and free of sealants that may out gas.

Figure 7C:
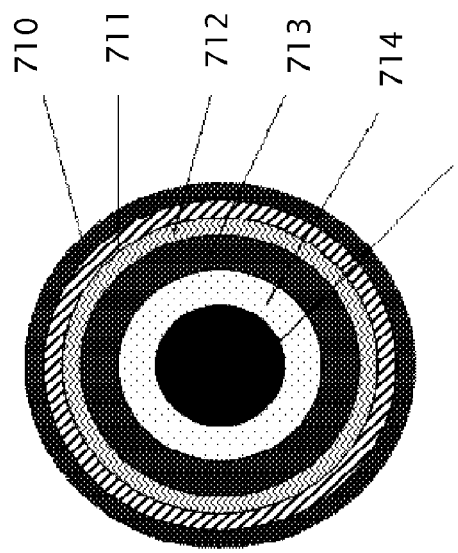
FIG. 7C schematically shows multiple rings on a Faraday ion detector.
Figure 7B:
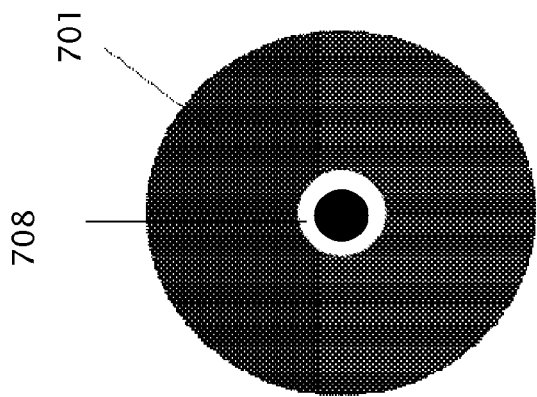
FIGS. 7A and 7B schematically shows the shape of ion outlets from ionization source.
Figure 7A:
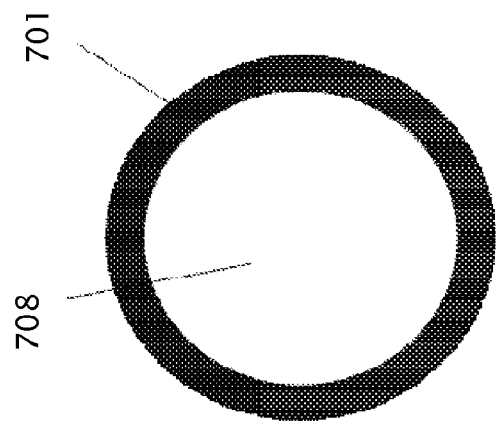

With the unique RC-IMS design, multiple coils could be used to construct a two dimensional IMS with the ions drift in both axial and radius direction. In this configuration, the inner coil has a voltage offset from the outer coil. FIG. 7 shows some components that are related to the two dimensional separation of the RC-IMS. In most of the IMS, reactant ions are generated in the ionization source and product ions are formed in the reaction region. The ionization source and reaction region normally have a similar size opening as the drift tube diameter, as shown in FIG. 7A. In the RC-IMS design, the ions are pushed out of the ionization source 701 through a much smaller opening 708 as shown in FIG. 7B. After entering the drift region, the ions will not only drift down the drift tube, they are also pushed toward the coil under the effluence of the electric field. Therefore, ions with different mobility are detected on different Faraday detection rings, 710, 711, 712, 713, 714, and 715 (FIG. 7C). The two-dimensional separation effect of this simple spectrometer can improve the detector by specificity reducing the false alarm rate.

Non-radioactive ionization methods for the detector: The "ready to be implemented" non-radioactive ionization source is the corona discharged ionization method which has been well studied. Most corona discharge ionization generates similar ionic species comparable with Ni63 ionization methods. Suitable configurations of the corona ionization source can be implemented into the RC-IMS to be used for the trace detection handheld wand. There are several newer concepts of non-radioactive ionization methods that will also be considered to interface with the proposed IMS. For example, electron beam ionization.

Figure 8:
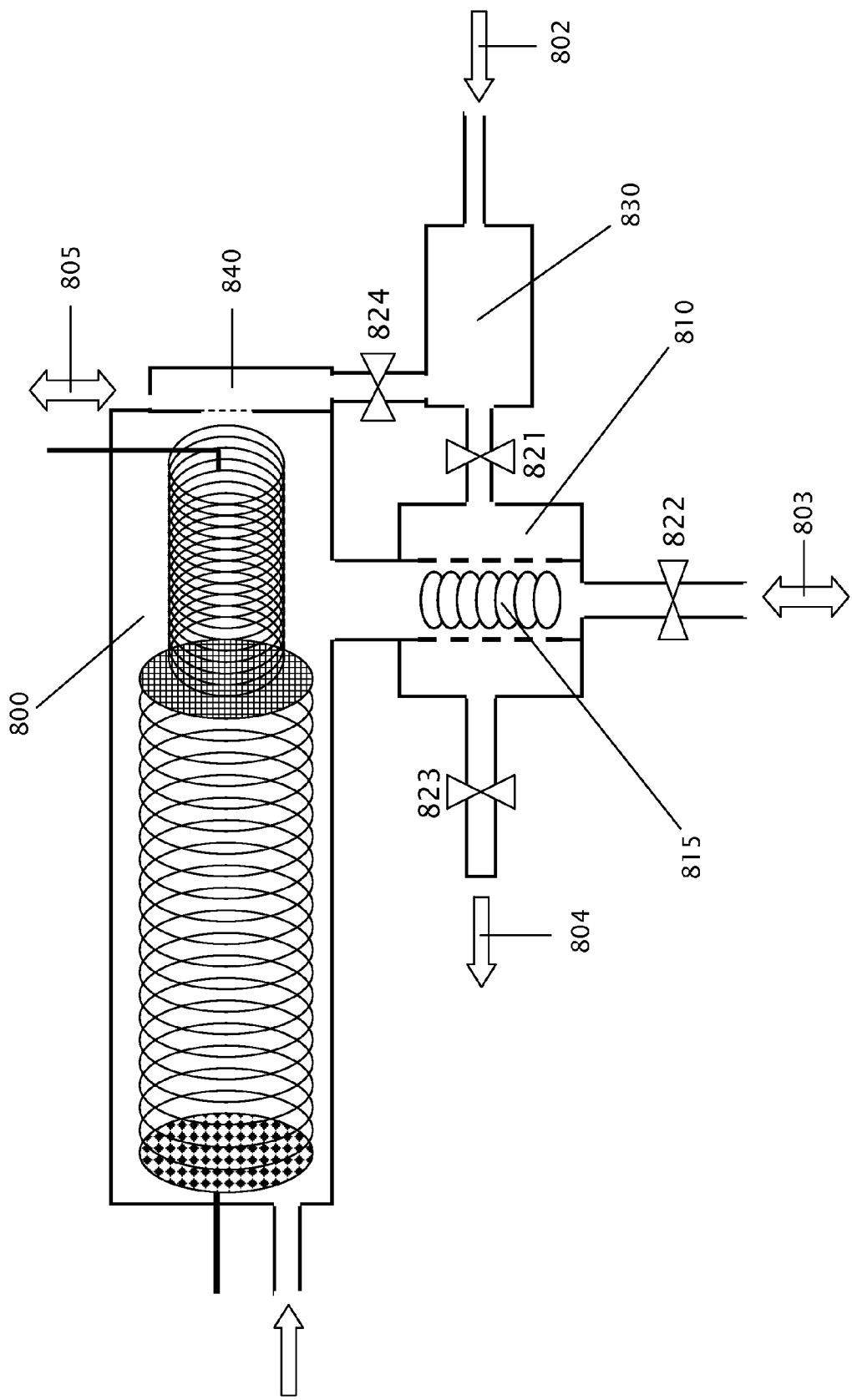
FIG. 8 schematically shows an alternative embodiment of sample preconcentration and desorption where preconcentrator can be made of a layer of coils.

FIG. 8 shows the apparatus of the ion mobility spectrometer with an alternative embodiment of the sample preconcentration and desorption. Instead of the flat filter like preconcentrator as disclosed above, the preconcentrator can be made from a single or plural layer of coils as shown in this figure. The coil could be made of any material that could be flash heated, e.g. resistive metal or alloy. The coil could be coated with chemicals that may have different affinities toward certain classes of chemicals, e.g. PDMS or modified PDMS. The coil is made with a designated pitch size that could trap/filter out certain sizes of the particles during preconcentration. Multiple coils could be made with different pitch sizes to achieve multiple step filtrations of particles of different sizes. Coils with smaller diameters can be arranged inside the larger ones, either coaxial or with an offside. If the coil at the upper stream of the fluid is to be filtered has a bigger pitch then the down stream ones, the larger particles can be filtered out first and then the smaller ones in turn.

As shown in the apparatus in the FIG. 8, when the sample flow 803 enters the preconcentrator chamber 810, it pass through the coils 815 (only single layer of coil is shown) and then is pumped away with the flow 804. The particles of different sizes are trapped on different layers of the coils. In general, the big pitch is made on the inside coils to capture larger particles and a smaller pitch is made on the outer coils to trap finer particles. The vapor sample can be trapped on any of the coils when interacting with the coil surface. They could be trapped without any affinitive coating if the preconcentrator is at a relative low temperature. During the sample preconcentration stage, valve 821 is closed, 822 and 823 are opened to allow flow to pass in a designated direction. In addition, the affinity layer coating material generally has higher electrical resistance compared to the coil material itself. Thus it can function as insulating layer when electrical current is passing through the coil for flash heating. The coating could be temperature resistive polymers, such as PDMS, or any other material that has a higher resistance than the material of the coil, functionalized silica based material is another example. Many sol-gel materials that could stand higher temperatures can also be coated on a metal coil after they are made into the right size and shape. Different coils or different sections of the coil can be coated with different materials to trap chemicals of different classes.

During the desorption process, a local chemical environment can be created to assist the desorption/evaporation process for the trapped samples of interest. To build up the certain level of chemical concentration is the desorption area, in this figure it is the preconcentration chamber 810, chemicals can be introduced as gas, liquid or solid as long as the chemicals can reach the trapped samples. The most convenient way to introduce such chemicals is bring them in as chemical vapor. The function of these chemicals is either to directly react with the samples that have been trapped or as catalysts that can convert the trapped sample into a form of interest. In addition, the same effect may be achieved not by introducing additional chemicals, but choosing right kind of material to build or coat the preconcentration coil. Under elevated temperature, the materials may behave as catalysts to achieve the same result of adding chemicals into the chamber.

To introduce additional chemicals to form a desired chemical environment for desorption, valve 822 is closed, 821 and 823 are open to redirect the source of the desorption flow. Gas flow 802 that passes through a chemical chamber 830 is introduced to the preconcentration chamber 810 during the desorption process. Chemical vapors that formed in the chemical chamber 830 are brought to the preconcentrated samples (that are trapped on the coils 815) to assist the desorption process. During the desorption process, the coils 815 are flash heated with a controlled temperature ramping speed to evaporate the trapped chemicals. In most applications, the doping chemicals through 821 are not needed for the desorption process. In this case, the desorption gas flow can be directed through 822. However, there are many thermal labile compounds that decompose before being evaporated to the gas phase. The doping of chemicals through 821 is to create a chemical environment in the preconcentrator chamber 810 to modify/control the reactions during the desorption. The products of desorption and reactions are brought into the detector for sub-sequential chemical analysis. The preconcentrator unit does not necessarily need to be used with an ion mobility spectrometer 800 as shown in FIG. 8. It could be interfaced to other analytical methods, such as a mass spectrometer. Optionally, the chemical chamber 830 can also be connected to a separate desorber for manual thermal desorption of collected samples. In many sample collection processes, the chemical can be preconcentrated on a filter paper like subtract using different methods, such as wiping a surface with the sample trap. In this case, the assisting chemicals are delivered to the thermal desorption heating plate chamber 840 via 824 when the sample trap is insert into the desorber. Flow 805 can either be gas outlet while the preconcentration chamber 810 is in use or gas inlet during a normal desorption process. In the later case, the assisting chemicals are not used and flow 803 is the purging flow for the spectrometer. As an example of the described trapping-desorption method, detection of peroxide based explosives is limited by the rapid decomposition during the desorption process. Using the method described in this invention, a clear decomposition path can be defined. For example, Hexamethylene Triperoside Diamine (HMTD) does not have a sensitive response in IMS systems because of the thermal decomposition, however, if the explosive is desorbed in the modified chemical environment that is doped with acidic vapor, a decomposition product can be predicted. In this specific case, the product is peroxy-bis-methanol [Jounal; Legler; CHBEAM; Chem. Ber.; 18; 1885; 3344] that could be sensitively detected by IMS in the negative ion mode. As it could be achieved by the apparatus described in this invention, thermal desorption of the trapped samples within chemically doped gas environment can be used to enhance desorption efficiency of the preconcentrator for explosive analysis.

What is claimed is:

1. A non-contact handheld multi-function interrogating apparatus comprising:
   (a) a handle that is connected to a front sampling region that comprises a particle sampling component and a metal detector in the same physical location of the front sampling region;
   (b) the particle sampling component is for actively collecting sample from a threat by searching an object without direct contact; and
   (c) the metal detector is for simultaneously searching metal objects while collecting sample of the first threat.

2. The non-contact handheld multi-function interrogation apparatus of claim 1, further comprises a wireless transmitter.

3. The non-contact handheld multi-function interrogation apparatus of claim 1, wherein the particle sampling component has at least one pair of facing air jet arrays to stimulate a particle from a targeted surface with a sheet-like impinging air flows.

4. The non-contact handheld multi-function interrogation apparatus of claim 3, further comprises a doping substance added to the sheet-like impinging air flows to assist the particle release from the targeted surface.

5. The non-contact handheld multi-function interrogation apparatus of claim 1, wherein the particle sampling component has a sample collector.

6. The non-contact handheld multi-function interrogation apparatus of claim 5, wherein the sample collector is a preconcentrator.

7. The non-contact handheld multi-function interrogation apparatus of claim 5, wherein the sample collector is a heated filter.

8. The non-contact handheld multi-function interrogation apparatus of claim 1, further comprises an onboard detector for analyzing the sample collected in the particle sampling component.

9. The non-contact handheld multi-function interrogation apparatus of claim 8, wherein the onboard detector is an ion mobility based detector.

* * * * *